United States Patent [19]
Faure et al.

[11] Patent Number: 6,143,273
[45] Date of Patent: Nov. 7, 2000

[54] THERAPEUTIC COMPOSITION CONTAINING ANTIBODIES TO SOLUBLE POLYPEPTIDE FRACTIONS OF LAG-3 PROTEIN

[75] Inventors: Florence Faure, Paris; Thierry Hercend, Charenton le Pont; Bertrand Huard, L'Haye les Roses; Frederic Triebel, Versailles, all of France

[73] Assignees: Institut Gustave Roussy, Villejuif Cedex; Institut National de la Santé et de la Recherche Medicale, Paris, both of France; Applied Research Systems ARS Holding N.V., Curacao, Netherlands Antilles

[21] Appl. No.: 09/058,555

[22] Filed: Apr. 13, 1998

Related U.S. Application Data

[62] Division of application No. 08/737,271, filed as application No. PCT/FR95/00593, May 5, 1995, Pat. No. 5,955,300.

[30] Foreign Application Priority Data

Jun. 5, 1994 [FR] France ................................ 94 05643

[51] Int. Cl.[7] ....................... A61K 51/00; A61K 39/395; C07K 16/28
[52] U.S. Cl. .................. 424/1.49; 424/139.1; 424/143.1; 424/152.1; 530/387.2; 530/387.9; 530/388.7; 530/388.73; 530/389.6; 530/391.3
[58] Field of Search ............................. 424/139.1, 152.1, 424/143.1, 1.49; 530/387.9, 388.7, 388.73, 389.6, 391.3, 387.2

[56] References Cited

FOREIGN PATENT DOCUMENTS

WO 91/10682  7/1991  WIPO.
WO 92/00092  1/1992  WIPO.

OTHER PUBLICATIONS

Biaxeras, E. et al. J. Exp. Med. 176(2):327–337, Aug. 1992.
Triebel, F. et al. J. Exp. Med. 171(5):1393–1405, May 1990.
Huard, B. et al. Intl. Con. Immunol. (Abstracts) p. 281, Aug. 1992.
Eilat, D. et al. Proc. Nat. Acad. Sci. (USA). 89(15):6871–6875, Aug. 1992.
DeSantes, K. et al. Cancer Research. 52:1916–1923, Apr. 1992.
Taetle, R. et al. J. Natl. Cancer Inst. 80(13):1053–1059, Sep. 1988.

*Primary Examiner*—Christina Y. Chan
*Assistant Examiner*—F. Pierre VanderVegt
*Attorney, Agent, or Firm*—Browdy and Neimark

[57] ABSTRACT

Soluble polypeptide fraction consisting of all or part of one at least one of the four immunoglobulin-type extracellular LAG-3 protein domains (amino acids 1–159, 160–230, 240–330 and 331–412 of the SEQ ID NO:1 sequence) or consisting of one peptide sequence derived from these domains by replacement, addition or deletion of one or more amino acids. The fraction of the invention has a specificity at least equal to that of LAG-3 in relation to its ligand.

5 Claims, 10 Drawing Sheets

THERAPEUTIC COMPOSITION CONTAINING ANTIBODIES TO SOLUBLE POLYPEPTIDE FRACTIONS OF LAG-3 PROTEIN

CROSS-REFERENCE TO RELATED APPLICATIONS

This application is a division of application Ser. No. 08/737,271, filed Dec. 24, 1996, now U.S. Pat. No. 5,955, 300, which is a §371 application of PCT/FR95/00593, filed May 5, 1995.

BACKGROUND OF THE INVENTION

1. Field of the Invention

The invention relates to soluble forms derived from the LAG-3 membrane protein which are useful as immunosuppressants, as well as antibodies capable of preventing the specific binding of the LAG-3 protein to MHC (major histocompatibility complex) Class II molecules as immunostimulants.

2. Description of the Related Art

In WO-A 91/10682, a protein designated LAG-3 has been described.

The LAG-3 protein is a protein selectively expressed by NK cells and activated T lymphocytes. Similarity of the amino acid sequence, the comparative exon/intron organization and the chromosomal localization shown that LAG-3 is related to CD4. The initial characterization of the LAG-3 gene has been described by TRIEBEL et al. (1).

The corresponding DNA codes for a type I transmembrane protein of 498 amino acids containing 4 extracellular sequences of the immunoglobulin type. LAG-3 is a member of the immunoglobulin superfamily.

The mature protein comprises 476 amino acids (SEQ ID NO:1) with a theoretical molecular weight of 52 kD. The extracellular region contains 8 cysteine residues and 4 potential N-glycosylation sites. By Western blot analysis, it was shown that LAG-3 inside PHA-blasts or activated NK cells has an apparent mass Mr of 70,000. After treatment with N-glycosidase F, a reduction in size to 60 kD was obtained, thereby demonstrating that native LAG-3 is glycosylated. Fuller details are described in WO-A 91/10682.

BAIXERAS et al., in J. Exp. Med. 176, 327–337 (2), have, in addition, described their finding that rosette formation between cells transfected with LAG-3 (expressing LAG-3 at their surface) and B lymphocytes expressing MHC Class II was specifically dependent on LAG-3/MHC Class II interaction.

Surprisingly, this ligand for MHC Class II was detected with higher levels on activated $CD8^+$ lymphocytes (MHC Class I-restricted) than on activated $CD4^+$ lymphocytes. In vivo, only a few disseminated $LAG-3^+$ cells (MHC Class II-restricted) were to be found in non-hyperplastic lymphoid tissue comprising the primary lymphoid organs, that is to say thymus and bone marrow. $LAG-3^+$ cells were to be found in hyperplastic lymphoid nodules and tonsils, as well as among peripheral blood mononuclear cells (PBMC) of patients receiving injections of high doses of IL-2.

These observations confirm that LAG-3 is an activation antigen in contrast to CD4 expressed in an subpopulation of resting lymphocytes and other cell types, in particular macrophages.

The MHC comprises Class I and Class II molecules which are membrane glycoproteins which present fragments of protein antigens to the T lymphocyte receptors (TCR). Class I molecules are responsible for the presentation to $CD8^+$ cytotoxic cells of peptides derived in large part from endogenously synthesized proteins, while Class II molecules present to $CD4^+$ helper lymphocytes peptides originating in the first place from foreign proteins which have entered the endocytic, that is to say exogenous, pathway. T helper lymphocytes regulate and amplify the immune response, while cytotoxic lymphocytes are needed to destroy cells irrespective of the tissues expressing "non-self" antigens, for example viral antigens. The mechanism of recognition involves intracellular signals leading to an effective activity of T lymphocytes.

It is apparent that, to initiate an immune response mediated by T ($CD4^+$) lymphocytes, the foreign antigens must be captured and internalized in the form of peptides by specialized cells, the antigen presenting cells (APC). The resulting antigenic peptides are re-expressed at the surface of the antigen presenting cells, where they are combined with MHC Class II molecules. This MHC Class II/peptide complex is specifically recognized by the T lymphocyte receptor, resulting in an activation of the T helper lymphocytes.

Moreover, animal models created by recombination techniques have made it possible to emphasize the part played in vivo by MHC Class II molecules and their ligands.

Thus, mice deficient in MHC Class II molecules (3) and possessing almost no peripheral $CD4^+$ T lymphocytes and having only a few immature $CD4^+$ lymphocytes in the thymus have proved to be completely incapable of responding to T-dependent antigens.

$CD4^{-/-}$ mutant mice (4) have a substantially decreased T lymphocyte activity but show normal development and function of the $CD8^+$ T lymphocytes, demonstrating that the expression of CD4 on the daughter cells and $CD4^+$ $CD8^+$ thymocytes is not obligatory for the development. Compared to normal mice, these CD4-deficient mice have a large amount of $CD4^-$ $CD8^-$ cells.

These doubly negative cells are restricted to MHC Class II and capable of recognizing the antigen.

When they are infected with Leishmania, these mice show a population of functional T helper lymphocytes despite the absence of CD4. These cells are restrictive to MHC Class II and produce interferon-γ when they are activated by the antigen. This indicates that the lineage of the T lymphocytes and their peripheral function need not necessarily depend on the function of CD4.

It is not recognized that the proteins encoded by MHC Class II region are involved in many aspects of immune recognition, including the interaction between different lymphoid cells such as lymphocytes and antigen presenting cells. Different observations have also shown that other mechanisms which do not take place via CD4 participate in the effector function of T helper lymphocytes.

These different observations underline the pivotal role played by MHC Class II and its ligands in the immune system.

Moreover, the importance is known of chimeric molecules composed of the extracytoplasmic domain of proteins capable of binding to ligands and a constant region of human immunoglobulin (Ig) chains for obtaining soluble forms of proteins and of cell receptors which are useful, in particular, as therapeutic agents.

Thus, soluble forms of CD4 have proven their efficacy in inhibiting an HIV infection in vitro in a dose-dependent manner.

Nevertheless, clinical trials with soluble CD4 molecules, in particular of CD4-Ig, have not enabled a significant decrease in viral titres to be demonstrated. Transgenic mice expressing up to 20 μg/ml of soluble CD4 in their serum were created. These mice showed no difference as regards their immune function relative to control mice. Hitherto, no direct binding to MHC Class II of molecules derived from CD4 has been reported. This strongly suggests that soluble CD4 molecules do not interact in vivo with MHC Class II molecules.

SUMMARY OF THE INVENTION

Surprisingly, the authors of the present invention have shown that soluble molecules containing different fragments of the extracytoplasmic domain of the LAG-3 protein were capable of binding to MHC Class II molecules and of having an immunosuppressant action.

The extracytoplasmic region of LAG-3 represented by the sequence SEQ ID No. 1 comprises the domains D1, D2, D3 and D4 extending from amino acids 1 to 149, 150 to 239, 240 to 330 and 331 to 412, respectively.

Thus, the subject of the invention is a soluble polypeptide fraction consisting of all or part of at least one of the 4 immunoglobulin type extracellular domains of the LAG-3 protein (amino acid 1 to 149, 150 to 239, 240 to 330 and 331 to 412 of the sequence SEQ ID No. 1), or of a peptide sequence derived from these domains by replacement, addition and/or deletion of one or more amino acids, and which possesses a specificity at least equal to or greater than that of LAG-3 for its ligand.

The present invention encompasses, in particular, soluble polypeptide fractions having a sequence derived from the native LAG-3 sequence originating from the well-known phenomenon of polytypy.

The soluble polypeptide fraction is characterized in that it comprises the peptide region of LAG-3 responsible for the affinity of LAG-3 for MHC Class II molecules.

The soluble polypeptide fraction comprises, in particular, a peptide sequence derived from these domains by replacement, addition and/or deletion of one or more amino acids, and which possesses a specificity equal to or greater than that of LAG-3 for its ligand, for example the whole of the first two immunoglobulin type domains of LAG-3, or the 4 immunoglobulin type domains of the extracytoplasmic domain of LAG-3.

Advantageously, the soluble polypeptide fraction is comprises of all or part of at least one of the four immunoglobulin type extracellular domains of the LAG-3 protein (amino acid 1 to 149, 150 to 239, 240 to 330 and 331 to 412 of sequence SEQ ID N° 1) comprising one or more of the arginine (Arg) rests at the positions 73, 75 and 76 of sequence SEQ ID N° 1 substituted with glutamic acid (Glu).

Preferably, the soluble polypeptide fraction comprises a loop in which the average position of the atoms forming the basic linkage arrangement is given by the position of amino acids 46 to 77 (SEQ ID No. 1) appearing in Table 1 or Table 2 or differs therefrom by not more than 5%.

The soluble polypeptide fraction advantageously comprises, in addition, the second immunoglobulin type extracellular domain (D2) of LAG-3 (amino acids 150 to 241).

Advantageously, the soluble polypeptide fraction comprises, besides the peptide sequence of LAG-3 as defined above, a supplementary peptide sequence at its C-terminal and/or N-terminal end, so as to constitute a fusion protein. The term "fusion protein" means a portion of any protein permitting modification of the physico-chemical features of the subfragments of the extracytoplasmic domain of the LAG-3 protein. Examples of such fusion properties contain fragments of the extracytoplasmic domain of LAG-3 as are defined above, bound to the heavy chain —CH2—CH3 junction region of a human immunoglobulin, preferably an isotype IgG4 immunoglobulin.

Such fusion proteins may be dimeric or monomeric. These fusion proteins may be obtained by recombination techniques well known to a person skilled in the art, for example a technique such as that described by Traunecker et al. (5).

Generally speaking, the method of production of these fusion proteins comprising an immunoglobulin region fused with a peptide sequence of LAG-3 as defined above consists in inserting into a vector the fragments of cDNA coding for the polypeptide regions corresponding to LAG-3 or derived from LAG-3, where appropriate after amplification by PCR, and the cDNA coding for the relevant region of the immunoglobulin, this cDNA being fused with cDNA coding for the corresponding polypeptide regions or derivatives of LAG-3, and in expressing after transfection the fragments cDNA in an expression system, in particular mammalian cells, for example hamster ovary cells.

The fusion proteins according to the invention may also be obtained by cleavage of a LAG-3/Ig conjugate constructed so as to contain a suitable cleavage site.

The subject of the invention is also a therapeutic composition having immunosuppressant activity comprising a soluble polypeptide fraction according to the invention. This composition will be useful for treating pathologies requiring immunosuppression, for example autoimmune diseases.

The subject of the invention is also the use of antibodies directed against LAG-3 or soluble polypeptide fractions derived from LAG-3 as are defined above, or fragments of such antibodies, in particular the Fab, Fab' and F(ab')$_2$ fragments, for the preparation of a therapeutic composition having immunostimulatory activity. "Immunostimulatory" means a molecular entity capable of stimulating the maturation, differentiation, proliferation and/or function of cells expressing LAG-3, that is to say T lymphocytes or active NK cells. The anti-LAG-3 antibodies may be used as potentiators of vaccines or immunostimulants in immunosuppressed patients, such as patients infected with HIV or treated with immunosuppressant substances, or be used to stimulate the immune system by elimination of self cells displaying abnormal behavior, for example cancer cells.

Immunostimulatory activity of anti-LAG-3 antibodies is surprising, inasmuch as anti-CD4 antibodies have an immunosuppressant action.

Such antibodies may be polyclonal or monoclonal; however, monoclonal antibodies are preferred. The polyclonal antibodies may be prepared according to well-known methods, such as that described by BENEDICT A. A. et al. (6). Monoclonal antibodies are preferred, on account of the fact that they are specific for a single epitope and yield results with better reproducibility. Methods of production of monoclonal antibodies are well known from the prior art, especially the one described by KOHLER and MILSTEIN. This method, together with variants thereof, are described by YELTON et al. (7).

The subject of the invention is also anti-idio-type antibodies directed against the antibodies according to the invention, which contain the internal image of LAG-3 and are consequently capable of binding to MHC Class II. Such antibodies may be used, in particular, as immunosuppressants, and, for example, in autoimmune pathologies.

The therapeutic compositions according to the present invention comprise soluble LAG-3 proteins or antibodies as are defined above, as well as a pharmaceutically acceptable vehicle. These compositions may be formulated according to the usual techniques. The vehicle can vary in form in accordance with the chosen administration route; oral, parenteral, sublingual, rectal or nasal.

For the compositions of parenteral administration, the vehicle will generally comprise sterile water as well as other possible ingredients promoting the solubility of the composition or its ability to be stored. The parenteral administration routes can consist of intravenous, intramuscular or subcutaneous injections.

The therapeutic composition can be of the sustained-release type, in particular for long-term treatments, for example in autoimmune diseases. The dose to be administered depends on the subject to be treated, in particular on the capacity of his/her immune system to achieve the desired degree of protection. The precise amounts of active ingredient to be administered may be readily determined by the practitioner who will initiate the treatment.

The therapeutic compositions according to the invention can comprise, in addition to soluble LAG-3 or the antibodies according to the invention, another active ingredient, where appropriate bound via a chemical bond to LAG-3 or to an antibody according to the invention. As an example, there may be mentioned soluble LAG-3 proteins according to the invention fused to a toxin, for example ricin or diphtheria toxoid, capable of binding to MHC Class II molecules and of killing the target cells, for example leukaemic or melanoma cells, or fused to a radioisotope.

DESCRIPTION OF THE PREFERRED EMBODIMENTS

Figure 1:
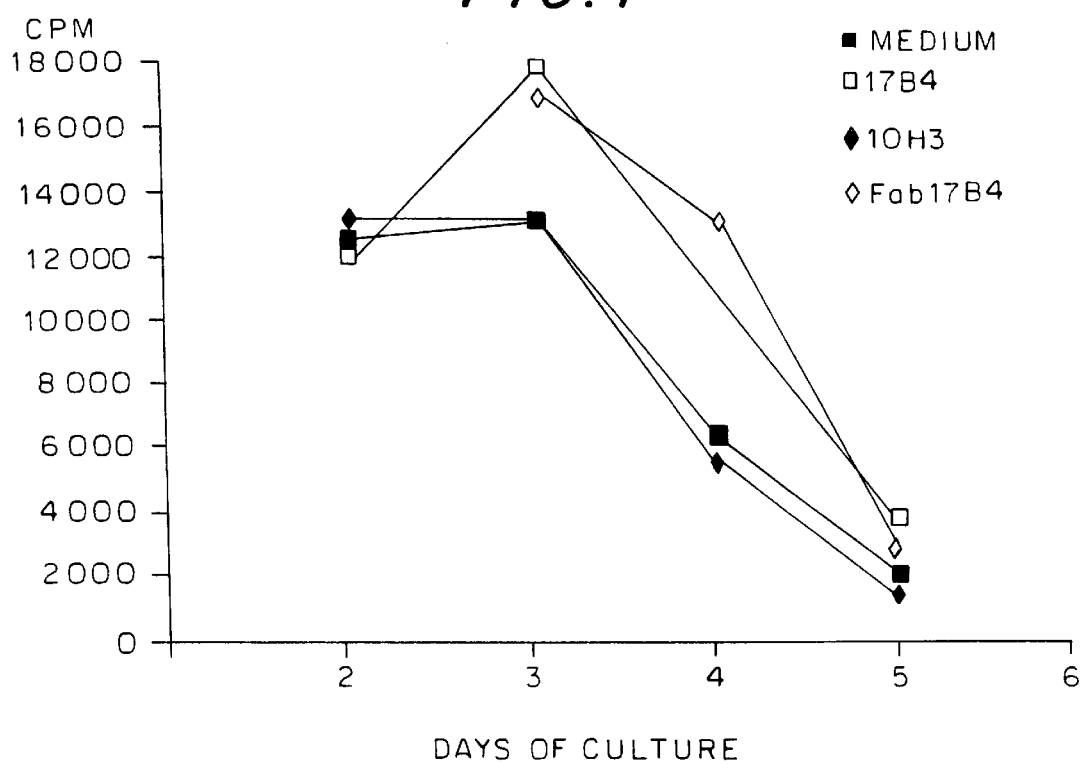
FIG. 1 shows a comparison of the proliferation of cells incubated with F(ab) fragments of 17B4 to the proliferation of T cells incubated with intact 17B4 monoclonal antibody.

The examples which follow, together with the attached reference figures, will illustrate the invention in greater detail.

EXAMPLE 1

Proliferation of active T lymphocyte lines in the presence of anti-LAG-3 monoclonal antibodies The anti-LAG-3 monoclonal antibodies used were 17B4, described in BAIXERAS et al. (2) and deposited at the CNCM under NO. I-1240 on Jul. 10, 1992, and 11E3, described in HUARD et al. (8).

These antibodies belong to the isotype IgG1. These antibodies were tested for their biological effects on activated T lymphocytes, stimulated by specific antigenic peptides or processed antigens presented by MHC Class II molecules expressed by autologous antigen presenting cells, expressing LAG-3.

An anti-CD48 monoclonal antibody designated 10 H3 was used as irrelevant IgG1 antibody (negative control).

The saturating concentrations of anti-LAG-3 and anti-CD48 antibodies were determined by immunofluorescence on PHA (phytohaemagglutinin)-blasts and cell lines transformed by Epstein-Barr virus (EBV). In the proliferation tests, the monoclonal antibodies were added in the proportion of 5 times the saturating concentration.

The T lymphocyte lines used were, on the one hand the clone 154 derived from peripheral blood lymphocytes, raised against a peptide mimicking an influenza haemagglutinin (HA) fragment having an amino acid sequence extending from amino acid 306 to 329 (p20 peptide), and on the other hand the clone 28, a T lymphocyte clone derived from peripheral lymphocytes of a single human donor, raised against diphtheria toxoid (DT). The antigen presenting cells (APC) corresponding to clone 154 were EBV-transformed B lymphocytes of the same donor (DR3/DR11) as T 154. The antigen presenting cells corresponding to clone 28 were EBV-transformed B lymphocytes of the same donor. This clone was restricted to HLA DR7.

For clone 154, the APC ($5 \times 10^6$) were incubated at 37° C. for one and a half hours with variable doses of the p20 peptide, then washed and irradiated (10,000 rad). The cells were plated out on 96-well microtitration plates at the same time as the clone 154 cells ($0.5 \times 10^5$ to $10 \times 10^5$ cells/ml) in a 3:1 ratio. For clone 28, the responding cells/stimulating cells ratio was 1.

The HLA DR7/EBV APC cells were either treated with mitomycin or irradiated, then added to the T lymphocytes in the presence of DT (which remained in the culture). The final concentration of clone 28 cells was 100,000 cells/ml.

[³H]Thymidine (1 μCi/well) was added at varying time intervals from day 2 to day 10 of culture.

Each experiment was carried out in triplicate.

The results were expressed as the mean cpm and after subtraction of the cpm found in the negative control (T lymphocytes cocultured with APC unladen with immunogens). The proliferation tests were carried out on 96-well plates. The absorption of tritiated thymidine in the individual 200 μl wells were measured after adding 1 μCi of thymidine for the last 18 hours of culture. The results were expressed in the form of the mean of 3 tests. The standard deviation was usually less than 12% (a little more in the case of ovary low cpm measurements). Moreover, mixed culture (clone 154/APC) supernatants were combined, filtered through 0.22 μm membranes, divided into samples and frozen at −20° C. until the time of titration using commercial immunoassay kits: Immunotech IL-2 and INF-α titration kit, Genzyme IFN-γ kit and Cayman Chemicals IL-4 kit.

A dose determination study was carried out to establish the proliferation profiles of clone 154 brought into contact with the p20 specific antigen at varying concentrations and in the presence or absence of anti-LAG-3 monoclonal antibodies or irrelevant monoclonal antibodies (negative control).

The individual results of 16 separate tests showed that, irrespective of the concentration of added antigen, the initial point up to the peak of proliferation was not modified, but a significant prolongation of the proliferation of T lymphocytes incubated with the anti-LAG-3 monoclonal antibodies was observed systematically. Fab fragments of the monoclonal antibody 17B4 were prepared and used in a test of proliferation of clone 154. The proliferation profile of T lymphocytes activated by the antigen with the 17B4 Fab fragments (15 μg/ml) was similar to that of cells incubated in the presence of whole 17B4 monoclonal antibody (40 μg/ml) (FIG. 1). These results show that the observed biological effects are not attributable to a non-specific reaction induced by the Fc region of the anti-LAG-3 monoclonal antibodies.

Similar results were obtained with the 11E3 anti-LAG-3 monoclonal antibodies.

Figure 2:
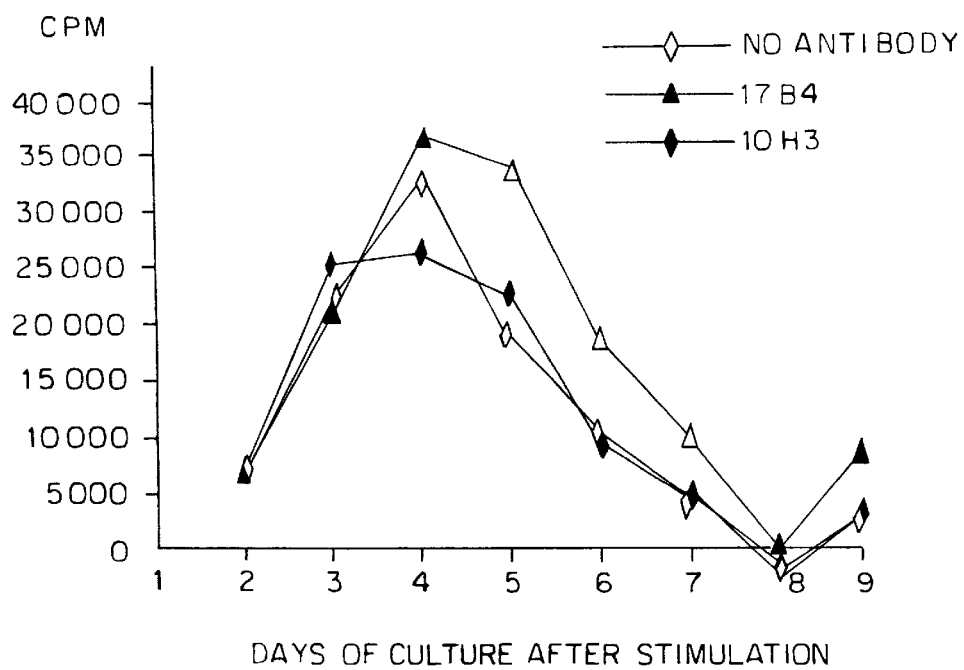
FIG. 2 shows the proliferation of Clone 28 in response to tetanus toxoid when co-cultured with 17B4 or control antibody 10H3.

Clone 28 was also stimulated with the antigen (tetanus toxoid 10 μg/ml) in the presence of 17B4 monoclonal antibodies after coculture with the corresponding APC in the presence of DT. The results are shown in FIG. 2.

The effects of the anti-LAG-3 monoclonal antibodies observed with clone 28, namely the prolongation of proliferation, are similar to those observed with clone 154.

Tests were carried out designed to measure the miscellaneous cellular events occurring after the antigenic stimulation of clone 154 cells incubated in the presence of anti-LAG-3 monoclonal antibodies.

The cells were harvested during conventional antigenic stimulation of clone 154 in the presence of anti-LAG-3 or anti-CD48 monoclonal antibodies or in the absence of antibodies, and tested for the expression of LAG-3 and CD25 transmembrane receptors, and samples of culture supernatants were collected at different time intervals after stimulation and tested for the presence of IFN-γ, TNF-α, IL-4 and IL-2.

Two-colour direct immunofluorescence tests (anti-CD3 monoclonal antibodies and anti-CD25 monoclonal antibodies) showed that IL-2 receptors were weakly but significantly increased 5 days after the antigenic stimulation. Similar tests with anti-CD3 and 11E3 (anti-LAG-3) monoclonal antibodies showed that LAG-3 was overexpressed from the day following activation onwards. In addition, the secretion of IL-2, IL-4, IFN-γ and TNF-α was also modulated by incubation with anti-LAG-3 monoclonal antibodies, thus showing that different cellular events are modified by the presence of anti-LAG-3 monoclonal antibodies and that some events already take place 24 hours after stimulation.

These results show indirectly that LAG-3 plays a regulatory role for $CD^{4+}$ cells. The fact that anti-LAG-3 monoclonal antibodies increase proliferation, and hence act as immunopotentiators, suggest that LAG-3 is involved in the "deactivation" of $CD4^+$ T lymphocytes with a negative role of LAG-3 on the antigen-dependent stimulation.

EXAMPLE 2

Transient expression of LAG-3 fusion proteins

Soluble proteins derived from LAG-3 were obtained by a recombinant DNA technique using suitable vectors comprising DNA coding for LAG-3 and DNA coding for an immunoglobulin fragment. The transient expression system consisted of transfected Cos cells. This system makes it possible to produce several mg of recombinant fusion proteins. Recombinant DNA techniques were carried out as described by MANIATIS et al. (22). The modifications were made as recommended by the manufacturer.

Construction of LAG-3 D1–D4 Ig and LAG-3 D1D2 Ig

Fragments coding for the D1D2 or D1–D4 regions were amplified (30 cycles) from a fragment of cDNA (FDC sequence) encompassing LAG-3 cDNA (TRIEBEL et al., (1)), using Taq polymerase free from 5'-endonuclease activity and relatively resistant to an exposure to very high temperature; the amplification was followed by a denaturation at 98° C. (with a Perkin Elmer Cetus "DNA thermal cycle"). Specific primers were used as recorded in the table below.

The resulting amplified fragments (739 bp and 1312 bp for LAG-3 D1D2 and LAG-3 D1–D4, respectively) were inserted into a pBS plasmid (Stratagene).

Figure 3:
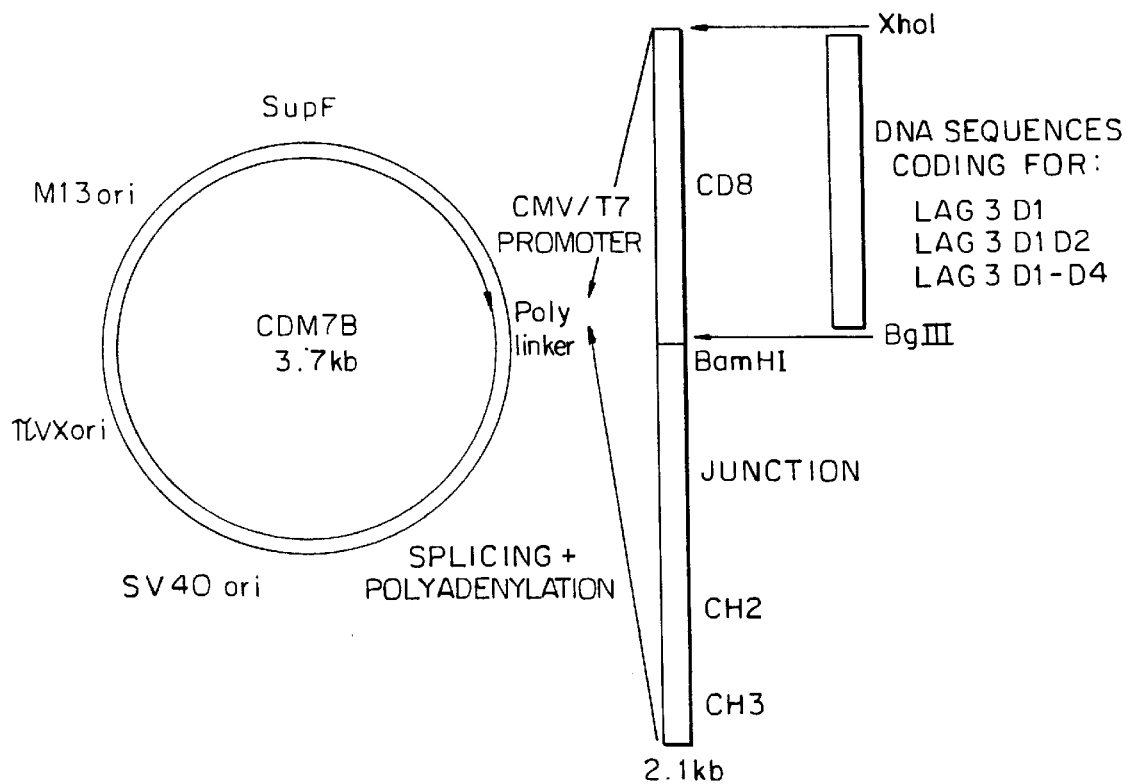
FIG. 3 shows the expression vector pCDM7 used for manufacturing the recombinant LAG-3 proteins and a recombinant CD8 immunoadhesin control.

Inserts were prepared after digestion with XhoI and BglII and introduced into the XhoI/BamHI sites of the vector pCDM7-CD8-IgG1 (pCDM7 being derived from pCDM8 marketed by Stratagene), as illustrated in FIG. 3, so as to exchange the DNA sequences coding for CD8 for those coding for the subfragments of LAG-3. The resulting expression vectors contained the sequences coding for D1D2 or D1–D4 fused to the DNA sequences coding for the —$CH_2$—$CH_3$ junction region of a human IgG1 chain.

TABLE 3

Primers used to amplify LAG-3 DNA sequences by PCR

| Primers used for amplification of the DNA | Resulting encoded subfragment fused with a subfragment Ig |
|---|---|
| Primer (5')<br>5' GCGCCTCGAGGCCCAGACCATAGGAGAGATGT 3' (SEQ ID NO:2)<br><br>coupling   untranslated   start of<br>site         5' sequences   translation<br><br>Primer (3')<br>5' GCGCAGATCTCTCCAGACCCAGAACAGTGAGGTTATACAT 3' (SEQ ID NO:3)<br><br>BglII coup-         End of D2<br>ling site | LAG-3 D1D2<br><br>from the leader sequence to amino acid 241 |
| Primer (5')<br>identical to LAG-3 D1D2<br><br>Primer (3')<br>5' GCGCAGATCTACCTGGGCTAGACAGCTCTGTGAA 3' (SEQ ID NO:4)<br><br>BglII coup-         End of D4<br>ling site | LAG-3 D1-D4<br><br>from the leader sequence to amino acid 412 |

CDM7 is a eukaryotic expression vector derived from the vectors developed by SEED et al. (10) for the cloning of DNA and its expression in *E. coli* and eukaryotic cells. CDM7 possesses the following features: (i) the human cytomegalovirus promoter for transient expression in mammalian cells; (ii) a viral origin of SV40 for an autosomal replication of mammalian cells expressing T antigen; (iii) π VX (type Col E1) as plasmid origin for a high copy number; (iv) a Sup F selection for resistance to ampicillin and tetracycline in Tet$^{amb}$ and Amp$^{amb}$ *E. coli* strains; (v) an origin of replication of M13 for the release of a single strand; (ix) a T7 RNA promoter; and (vii) a polylinker for an efficient cloning of heterologous DNA.

Transient expression in Cos cells

Cos cells (5×10$^6$) were transfected with 30 µg of DNA of suitable expression vectors (coding for either LAG-3 D1D2 Ig, or LAG-3 D1–D4 Ig, or CD8 Ig) by electroporation (200 V, 1500 µF, 30–40 msec) using a Cellject apparatus (Eurogentech, Liége, BE). The cells were plated out again and cultured on a medium containing 5% of foetal calf serum. The supernatants were withdrawn 6 days after transfection.

The synthesis of the resulting fusion proteins was analysed from the supernatants as well as from cell extracts of transfected cells, by Western blot analysis with the 17B4 monoclonal antibodies. Immunoreactive materials were observed in the supernatant of cells transfected with DNA coding for LAG-3 D1D2 Ig or LAG-3 D1–D4 Ig.

Concomitantly, a recombinant CD8 immunoadhesin (CD8 Ig) was obtained as negative control using the same expression system and the expression vector pCDM7-CD8 (FIG. 3).

The recombinant proteins LAG-3 D1D2 Ig, LAG-3 D1–D4 and CD8 Ig were purified by means of the standard method on protein A-Sepharose. The resulting material was analysed by SDS-PAGE, followed by Coomassie staining or a Western blot analysis using anti-human Ig antibody.

EXAMPLE 3

Production of soluble subfragments of LAG-3

In order to produce large amounts of recombinant proteins, a stable expression system comprising of transfected mammalian cells was developed. The host cells are anchorage-dependent hamster ovary (CHO) cells isolated from CHO cells deficient in dihydrofolate reductase (DHFR) and consequently necessitating glycine, a purine and thymidine for their growth. The pivotal role of DHFR in the synthesis of nucleic acid precursors, combined with the sensitivity of DHFR-deficient cells with respect to tetrahydrofolate analogues such as methotrexate (MTX), has two major advantages. Transfection of these cells with expression vectors containing the DHFR gene permits the secretion of recombinant DHFR-resistant clones, and the culturing of these cells on selective media containing increasing amounts of MTX results in amplification of the DHFR gene and the DNA associated therewith.

Construction of LAG-3 D1, LAG-3 D1D2, LAG-3 D1–D4

Fragments of DNA coding for the D1, D1D2 or D1–D4 regions were amplified using a PCR method identical to the one described previously, using the primers specified in the table below.

TABLE 4

Primers used for amplifying LAG-3 DNA sequences by PCR

| Primers used for amplification of the DNA | Resulting encoded subfragment |
|---|---|
| Primer (5') <br> 5' CGCC<u>GTCGAC</u>CGCTGCCCAGACCATAGGAGAG<u>ATG</u>TG 3' (SEQ ID NO:5) <br><br> SalI coupling site — untranslated 5' sequences — start of translation | LAG-3 D1 <br><br> from the leader sequence to amino acid 149 |
| Primer (3') <br> 5' GCGC<u>GTCGAC</u>TTACATCGAGGCCTGGCCCAGGCGCAG 3' (SEQ ID NO:6) <br><br> SalI coupling site — End of D1 | |
| Primer (5') <br> identical to LAG-3 D1 | LAG-3 D1D2 |
| Primer (3') <br> 5' GCGC<u>GTCGAC</u>TTAACCCAGAACAGTGAGGTTATAC 3' (SEQ ID NO:7) <br><br> SalI coupling site — End of D2 | from the leader sequence to amino acid 239 |
| Primer (5') <br> identical to LAG-3 D1 | LAG-3 D1-D4 |
| Primer (3') <br> 5' GCGC<u>GTCGAC</u>TTAACCTGGGCTAGACAGCTCTGTG 3' (SEQ ID NO:8) <br><br> SalI coupling site — End of D4 | from the leader sequence to amino acid 412 |

The resulting amplified fragments were digested with SalI and inserted into the SalI site of pUC 18 (Stratagene).

Figure 4:
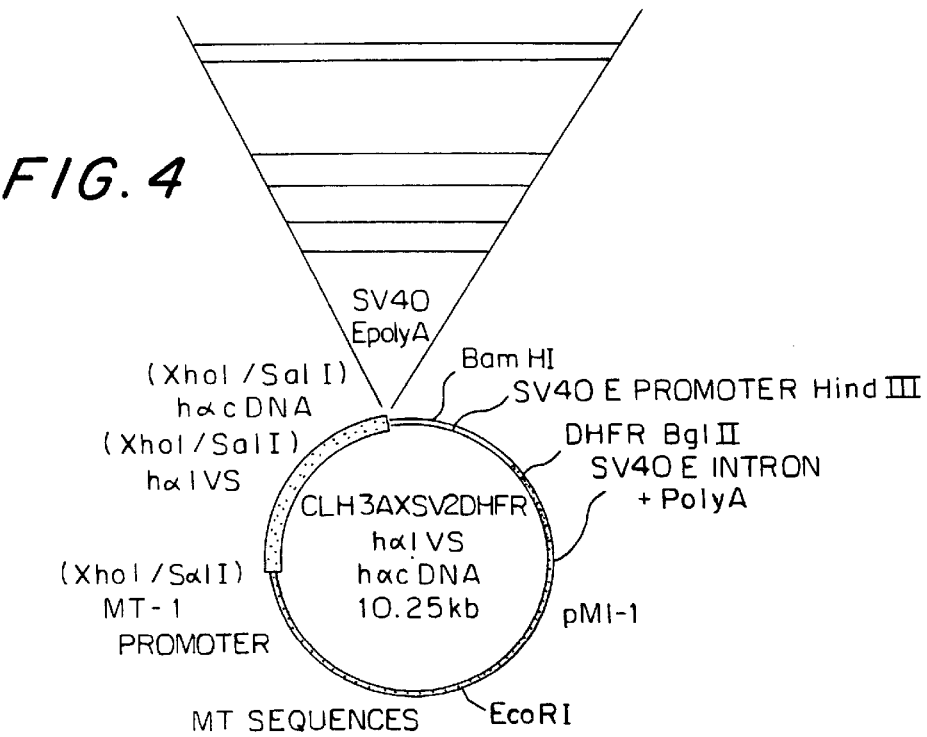
FIG. 4 shows the pCLH3 AXS DHFR hα IVS vector used to express amplified LAG-3 sequences.

The amplified sequences were verified, and the inserts subcloned into the expression vector pCLH3 AXS V2 DHFR hα IVS as described by COLE et al. (Biotechnology 11, 1014–1024, 1993) (FIG. 4).

This vector is a eukaryotic expression vector which is multifunctional for the expression cDNA and its amplification in eukaryotic cells. It possesses the following features: (i) the murine promoter of the metallothionein-1 gene and a polyadenylation sequence SV 40 (comprising a donor-acceptor splicing site) to bring about transcription of the gene of interest, (ii) a human intervening sequence A containing the donor-acceptor splicing site of the gene for the subunit of α glycoprotein for obtaining high levels of transcription of cDNA, (iii) the pML sequence containing the origin of replication of pBR 322 and a gene for resistance to ampicillin for bacterial amplification, and (iv) a DHFR transcription unit of SV 40 to bring about transcription of the sequences used for selection and amplification of the transfectants.

Stable expression in CHO cells

The expression vectors coding for LAG-3 D1, LAG-3 D1D2 and LAG-3 D1–D4 were used to transfect CHO DUKX cells, and these cells were cultured on a selective medium. Cells capable of multiplying under these conditions were combined and cultured on a medium containing increasing amounts of MTX. Levels of expression were measured by Western blot analysis using the 17B4 monoclonal antibody. Clones producing high levels of recombinant soluble molecules derived from LAG-3 were propagated in bioreactors, and the material derived from LAG-3 was purified by ion exchange chromatography and immunoaffinity.

Western blot analyses revealed, in supernatants of cells transfected with expression vectors coding for LAG-3 D1, LAG-3 D1D2 and LAG-3 D1–D4, bands with apparent Mr values of 15 to 18 kD, 34–36 kD (doublets) and 55 kD (2 possible bands). The respective Mr values of these immunoreactive materials corresponded to the expected Mr values of glycosylated LAG-3 D1 Ig (139 amino acids and a putative N-glycosylating site), glycosylated LAG-3 D1D2 Ig (239 amino acids containing 3 glycosylation sites) and glycosylated LAG-3 D1–D4 (412 amino acids containing 4 glycosylation sites).

EXAMPLE 4

Specific binding of LAG-3 Ig to cells expressing MHC Class II

The reactivity of the monoclonal antibodies and of LAG-3 D1–D4 was studied by indirect immunofluorescence. Target cells ($4 \times 10^5$) were incubated for 30 minutes at 4° C. in the presence of LAG-3 D1–D4 Ig, CD8 Ig, a murine monoclonal antibody, (949) anti-human MHC Class II (DR, DP, DQ) conjugated to FITC (isothiocyanate fluoride) from a Coulter clone, or murine Ig-FITC: an irrelevant immunoglobulin G conjugated to FITC. The cells were washed and incubated at 4° C. for 30 minutes with either a goat anti-human Ig polyclonal F(ab')$_2$ conjugated to fluorescein or a goat anti-mouse Ig polyclonal antibody conjugated to fluorescein (Coulter clone).

To confirm the LAG-3/MHC Class II binding, LAG-3 D1–D4 Ig was incubated with MHC class II-positive or -negative cells. Four B lymphocyte lines expressing MHC Class II(L31, Phil EBV, Raji, Sanchez and Personnaz) were treated with anti-Class II monoclonal antibody 949, or the supernatants of Cos cells transfected with DNA coding either for LAG-3 D1–D4 or for CD8 Ig. The five cell lines expressing the different haplotypes of MHC Class II molecules were recognized by LAG-3 Ig in the same way as by the anti-Class II monoclonal antibodies (positive control), while the supernatant containing CD8 Ig (negative control) did not bind to these cell lines, as could be expected. Four MHC Class II-negative cell lines (CEM, RJ, HSB2, K562) were treated with the same reagents as above. None reacted, either with the anti-MHC Class II (negative control) or with LAG-3 D1–D4 Ig, showing that the binding of LAG-3 D1–D4 is specific to MHC Class II molecules.

Figure 8:
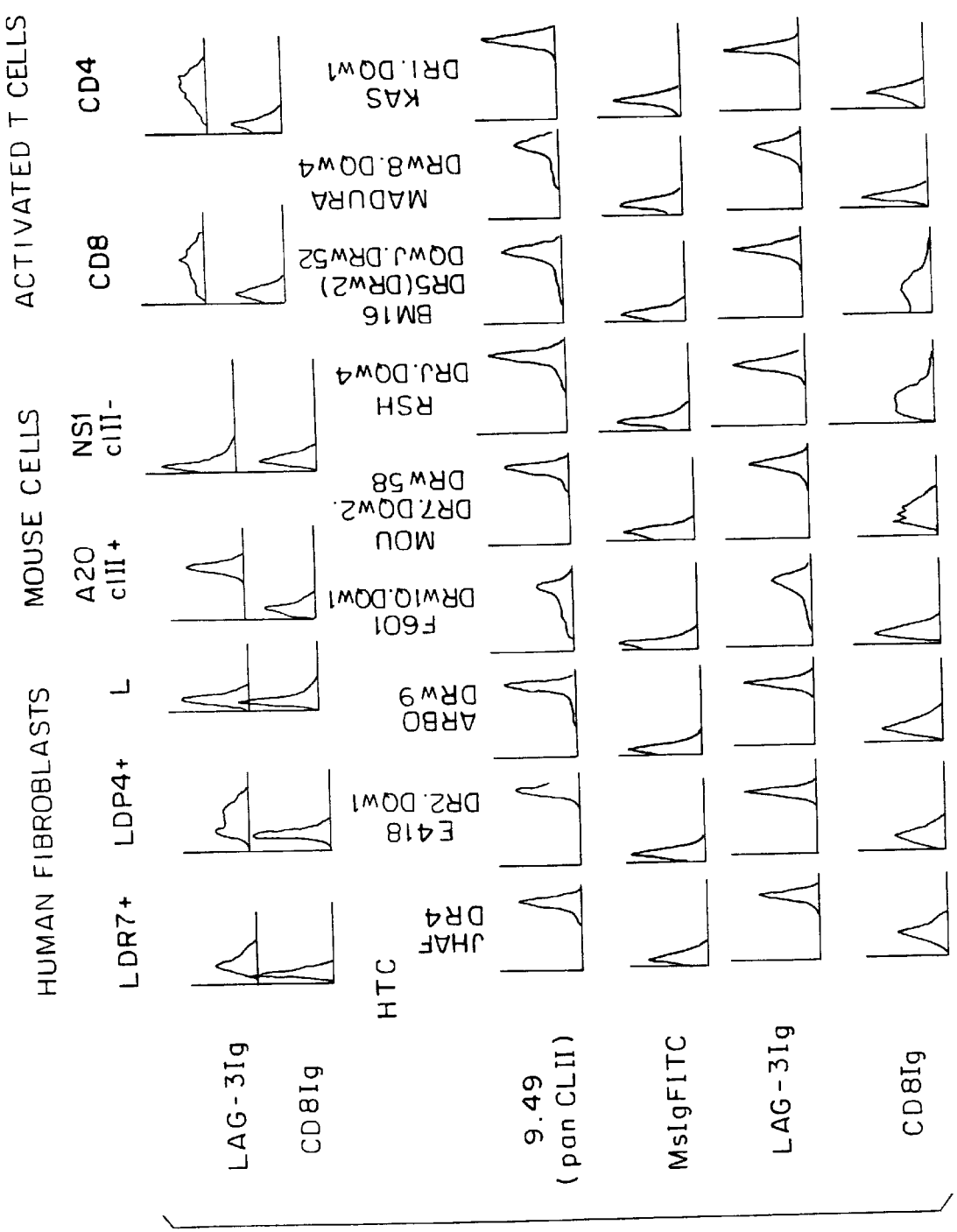
FIG. 8 shows the binding of LAG-3 to B cell lines expressing MHC class II haplotypes or human class II-transfected mouse cells.

Further experiments were carried out using (i) mouse fibroblasts transfected or otherwise with genes coding for human DR7 or human DP4, (ii) mouse cells expressing or otherwise MHC Class II molecules, (iii) activated human $CD4^+$ or $CD8^+$ cells, and (iv) T lymphocyte lines expressing the different haplotypes of MHC Class II molecules (FIG. 8).

Unlike CD8 Ig, LAG-3 D1–D4 Ig binds to all cells expressing MHC Class II as efficiently as the anti-MHC Class II monoclonal antibody 949. LAG-3 D1–D4 Ig binds to all DR and DP haplotypes tested, to human MHC Class II molecules expressed by transfected mouse cells, to murine MHC Class II molecules and also to MHC Class II molecules expressed by $CD4^+$ or $CD8^+$ lymphocytes.

These results represent for the first time proof that soluble molecules derived from a ligand for MHC Class II are capable of binding to cells expressing MHC Class II.

Similar experiments showed that LAG-3 D1D2 bound to cells expressing MHC Class II in as specific a manner and with the same efficiency as LAG-3 D1–D4.

Binding activity of LAG-3Ig and cellular distribution of ligands for LAG-3Ig

The capacity of this immunoadhesin to bind to cell ligands is measured using a fluorescein-labelled goat serum directed against human immunoglobulins.

Figure 9:
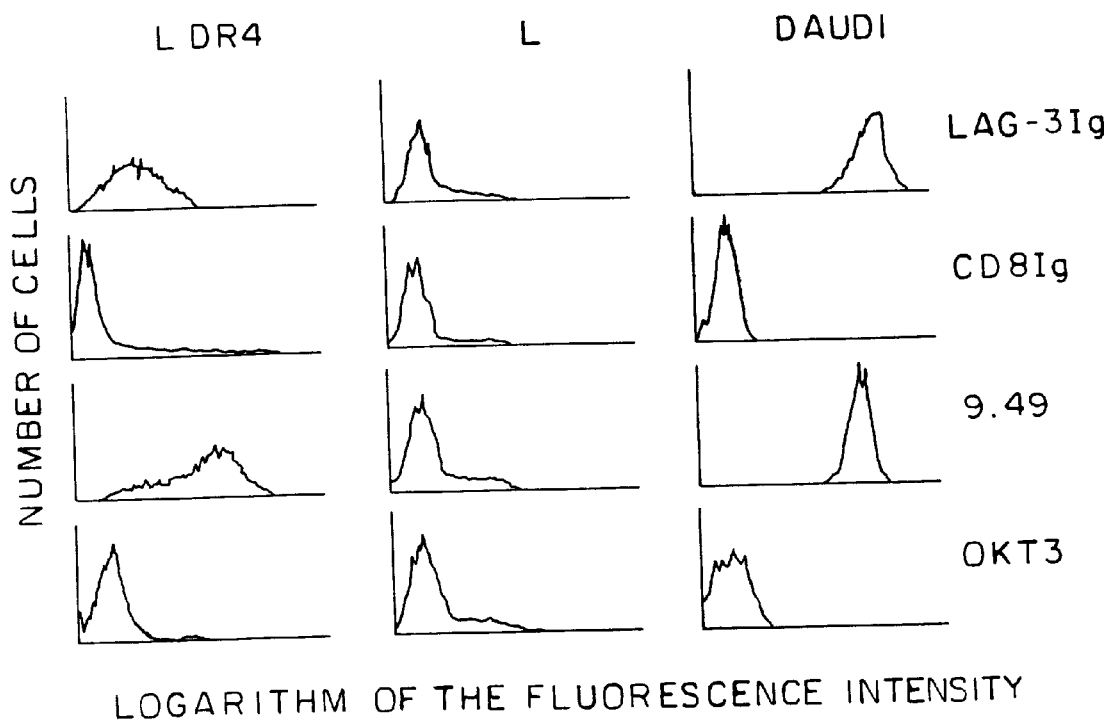
FIG. 9 shows the binding of LAG-3 Ig to MHC Class II expressing Daudi cells.

In these experiments, the target cells are first incubated with a human monoclonal antibody or an immunoadhesin for 30 min at 4° C. in RPMI 1640 containing 10% of FCS (foetal calf serum). The cells are then incubated with an FITC-labelled goat anti-mouse immunoglobulin serum (Coulter) for the murine monoclonal antibodies or with an FITC-labelled goat anti-human immunoglobulin serum (Tago) for the immunoadhesins. The fluorescence is measured after two washes, analyzing 3,000 cells with an Elite cytometer (Coultronics, Hialeah, Fla.). FIG. 9 shows the degrees of binding of LAG-3Ig, CD8Ig, antibody 949 or antibody OKT3 (anti-CD3, ATCC), represented by the number of cells counted as a function of the logarithm of the measured fluorescence intensity.

LAG-3Ig binds to mouse fibroblasts transfected for the gene for the HLA $DR_4$ molecule, and does not bind to untransfected cells. CD8Ig is capable of binding to HLA $DR_4^+$ fibroblasts under the same conditions.

The cellular distribution of the ligands for LAG-3Ig was evaluated on a cell population sample by immunofluorescence.

LAG-3Ig is visualized on all positive Class II cells tested, including B cell lines transformed by Epstein-Barr virus (derived from genetically unrelated donors, including 10 homozygous lines of $DR_1$ to $DR_{10}$ typing), as well as on activated T and NK cells.

FIG. 9 shows, by way of example, the binding of LAG-3Ig to Daudi cells which are positive for Class II antigens.

The means fluorescence intensity with LAG-3Ig is similar to that observed with antibody 949 which is specific for Class II antigens. The binding of LAG-3Ig to $DR_4$ (FIG. 9), $DR_2$, $DR_7$ and DPw4 (not shown) expressed at the surface of mouse fibroblasts is, in contrast, weaker than that observed for antibody 949.

No binding is detected on cell lines which are negative for Class II antigens of T origin (peripheral blood T cells, CEM, HSB2, REX lines), of B origin (RJ 2.2.5 line) or of non-lymphoid origin (human lines, K562 of erythromyoloid origin and line originating from melanoma cells (not shown).

Moreover, LAG-3Ig binds to xenogeneic Class II molecules of the MHC, such as the antigens expressed by mouse lymphoma A 20 and the monkey Classes II expressed by phytohaemagglutinin-stimulated blasts (data not shown).

Figure 10:
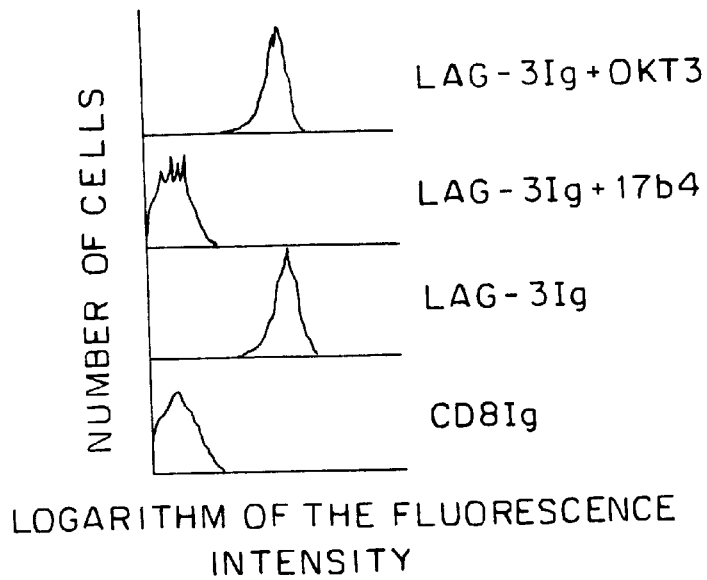
FIG. 10 shows that preincubation of HLA class II expressing cells with 17B4 inhibiting LAG-3 Ig binding.

The specificity of binding of LAG-3Ig was also verified using the monoclonal antibodies 17B4, whose capacity to block LAG-3/MHC Class II interactions in cell adhesion tests was demonstrated beforehand (FIG. 10).

In these experiments, the LAG-3Ig molecules are preincubated for 30 minutes at 4° C. either with medium alone, or with 17B4 (1 mg/ml), or with OKT3 (1 mg/ml), before being brought into contact with Daudi cells.

FIG. 10 shows that a preincubation of LAG-3Ig with 17B4 inhibits the binding to Class $II^+$ cells, whereas no inhibition is detected with the OKT3 control.

EXAMPLE 5

Inhibition of LAG-3/MHC Class II interaction by soluble fragments of LAG-3

The inhibition of LAG-3/MHC Class II interaction by the soluble fragments of LAG-3 may be observed directly in relation to the binding of LAG-3Ig by Class II MHC molecules, by competitive experiments with the soluble fragments.

To verify whether the soluble LAG-3$D_1D_2$ fragments produced by CHO cells could displace the binding of immunoadhesins derived from LAG-3, the following tests were carried out:

Daudi cells are incubated with soluble LAG3-$D_1D_2$ fragments so as to permit the binding of these molecules to the MHC Class II antigens expressed at the surface of the Daudi cells.

In a second step, the cells are incubated in the presence of LAG-3$D_1D_4$Ig in dimeric form or LAG-3$D_1D_2$Ig in monomeric form.

The binding of these immunoadhesins derived from LAG-3 is measured using a goat anti-human Ig F(ab')$_2$ conjugated to fluorescein (GAH-FITC).

The control groups are represented by Daudi cells incubated with dimeric LAG-3$D_1D_4$Ig or monomeric LAG-3$D_1D_2$Ig without preincubation with the soluble LAG-3$D_1D_2$ fragments.

The results are recorded in Table 5, which shows that the soluble LAG-3$D_1D_2$ fragments are capable of displacing the immunoadhesins derived from LAG-3 in mono- or dimeric form.

TABLE 5

| Reactants | Detection | Mean fluorescence | Conclusion |
|---|---|---|---|
| — | GAH-FITC | 0.3 | GAH does not interfere |
| Dimeric LAG-3D1D4Ig | GAH-FITC | 20.8 | The binding of CHO/LAG-3D1D2 |
| CHO/LAG-3D1D2, then dimeric LAG-3D1D4Ig | GAH-FITC | 8.5 | inhibits the binding of dimeric LAG-3D1D4Ig (58%) |
| Monomeric LAG-3D1D2Ig | GAH-FITC | 62.5 | The binding of CHO/LAG-3D1D2 |
| CHO/LAG-3D1D2, then monomeric LAG-3D1D2Ig | GAH-FITC | 10.9 | inhibits the binding of monomeric LAG-3D1D2Ig (27%) |

These data confirm that the soluble LAG-3D1D2 fragments bind to MHC Class II molecules.

Inhibition of LAG-3/MHC Class II and CD4/MHC Class II interaction

Rosette formation between Cos cells transfected with wild-type LAG-3 and B lymphocytes transformed with EBV expressing MHC Class II molecules was demonstrated by BAIXERAS et al. (2). This interaction is inhibited both by anti-LAG-3 and anti-MHC Class II monoclonal antibodies.

The method described in this publication was modified by replacing the visualization and counting of Cos cells binding to B lymphocytes by counting the radioactivity remaining after incubation of $^{51}$Cr-labelled B lymphocytes with Cos cells expressing LAG-3 (binding assay).

The possible inhibitory effects of soluble molecules derived from LAG-3 on LAG-3/MHC Class II interaction, and also on CD4/MHC Class II interaction, were studied.

Cos cells transfected with a suitable expression vector (coding for wild-type LAG-3 or for CD4). Two days later, the Cos cells were treated with trypsin and plated out again on the basis of 0.05×10$^6$ cells/well on flat-bottomed 12-well tissue culture plates. 24 hours later, $^{51}$Cr-labelled Daudi cells (5.5×10$^6$) were incubated on this monolayer of Cos cells (final vol.: 1 ml) for 1 hour. The target B cells were then aspirated off and the wells washed 5 to 7 times, gently adding 1 ml of medium dropwise. The edges of the wells were washed by suction using a Pasteur pipette. The remaining cells were lysed with 1 ml of PBS, 1% Triton for 15 minutes at 37° C. The lysates were centrifuged at 3000 rpm for 10 minutes, and 100 μl of the resulting supernatant were counted.

LAG-3 D1–D4 Ig was used to inhibit LAG-3/MHC Class II and CD4/MHC Class II interaction in the $^{51}$Cr binding assay. Human CD8 Ig and IgG1 were tested in parallel and used as negative controls.

Figure 5:
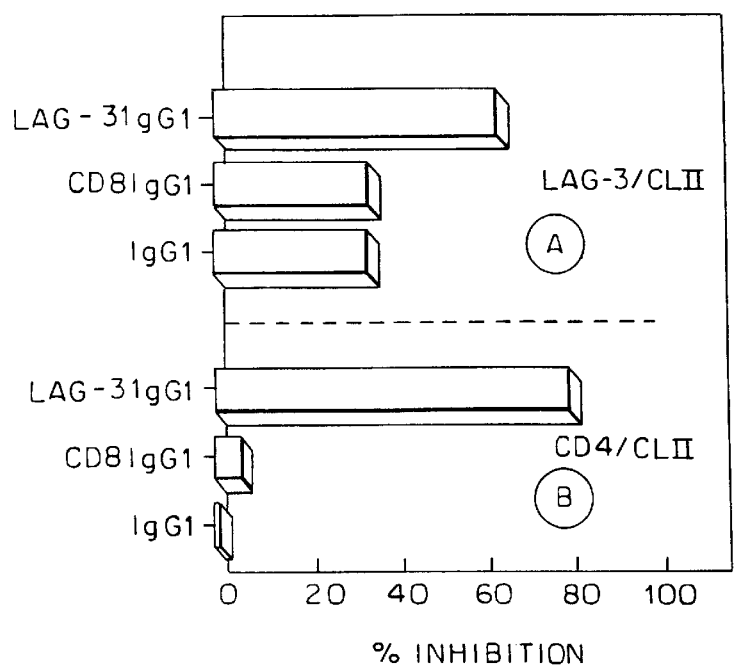
FIG. 5A shows the inhibition of MHC Class II interaction with LAG-3 by recombinant LAG-3 D1–D4 and FIG. 5B shows the potential inhibition of MHC Class II interaction with CD4.

A significant inhibition of LAG-3/Class II interaction by LAG-3 D1–D4 Ig was detected (FIG. 5A). However, the LAG-3/MHC Class II interaction can be partially and non-specifically inhibited by human CD8 Ig and IgG1. Moreover, LAG-3 Ig proved to be a potential inhibitor of CD4/Class II interaction (FIG. 5B) under experimental conditions in which CD4/MHC Class II interaction was not modified by human CD8 Ig or IgG1. This suggests that LAG-3/Class II interaction is weaker than CD4/MHC Class II interaction. These results represent the first proof of a possible competition of soluble molecules in an interaction of MHC Class II with its ligands.

EXAMPLE 6

Immunosuppressant activity of LAG-3 D1–D4 Ig

Functional tests were performed using the proliferation tests described above for the biological activity of the anti-LAG-3 monoclonal antibodies.

Figure 6:
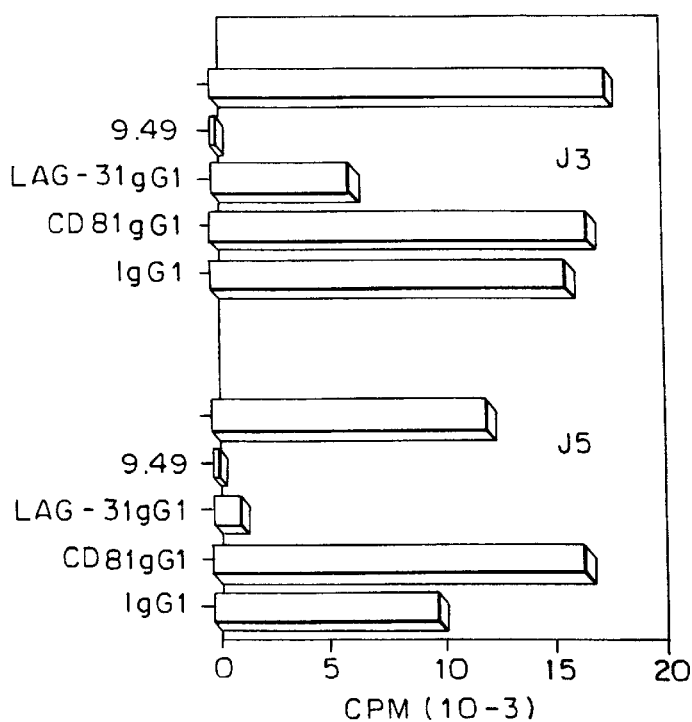
FIG. 6 shows the inhibition of Clone 28 proliferation by recombinant LAG-3 D1–D4.
Figure 7:
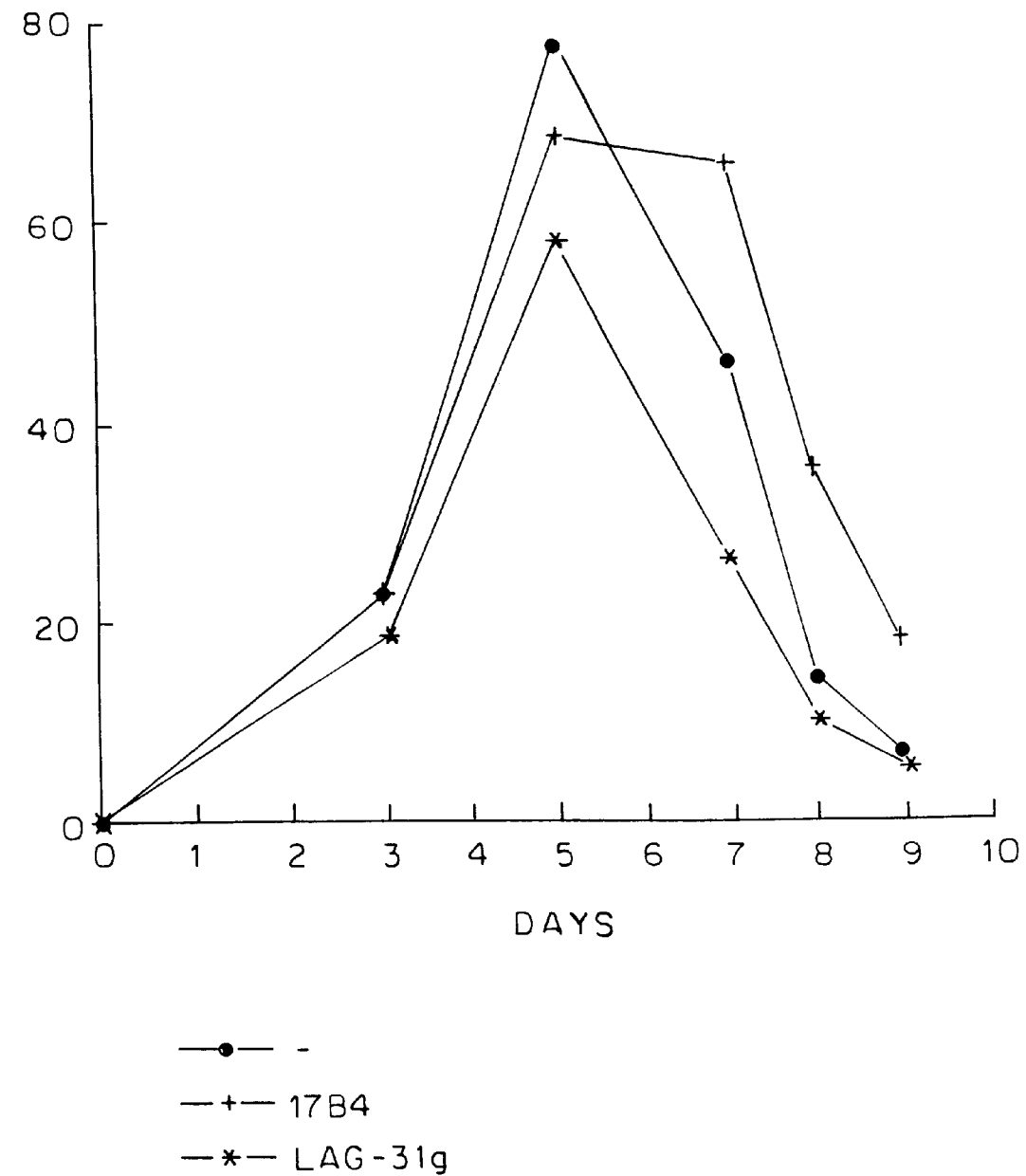
FIG. 7 shows the inhibition of Clone 154 proliferation by LAG-3 Ig.

3 days and 5 days (D3 and D5) after antigenic stimulation, LAG-3 D1–D4 Ig showed a strong inhibition of the proliferation of clone 28, while human CD8 Ig and IgG had no effect (FIG. 6). Similar experiments were carried out with clone 154 (FIG. 7), and showed a partial inhibition in the presence of LAG-3 Ig. A control carried out with anti-LAG-3 monoclonal antibodies had the reverse effects, as observed previously.

A significant inhibition of the cell proliferation of cells incubated in the presence of LAG-3 D1–D4 Ig was also observed for clone 28.

These observations show that LAG-3 D1–D4 Ig is a potential immunosuppressant of the proliferation of T lymphocytes stimulated by an antigen, and indicate that LAG-3 might act as an "extinguisher" of the secondary immune response induced by activated CD4$^+$ T helper lymphocytes.

Role of LAG-3Ig in the negative regulation of the immune response of T cells

To demonstrate that a soluble form of LAG-3, mimicking the functions of the membrane molecule, could inhibit the activation of CD$_4^+$ T clones stimulated by an antigen, the following tests were carried out on clone T154: the T cells are incubated beforehand with a saturating amount of LAG-3Ig (100 nM). The cells are then washed twice with cold RPMI and incubated with 10 μg/ml of goat antibodies directed against human immunoglobulins (Tago) at 4° C. for 30 minutes.

After two more washes, the cells are resuspended in RPMI containing 10% of foetal calf serum and incubated for 2 hours at 37° C. before adding the signal. To couple ("cross-link") the monoclonal antibodies, a goat anti-mouse antibody at a concentration of 10 μg/ml (Tago) is used.

Figure 11A:
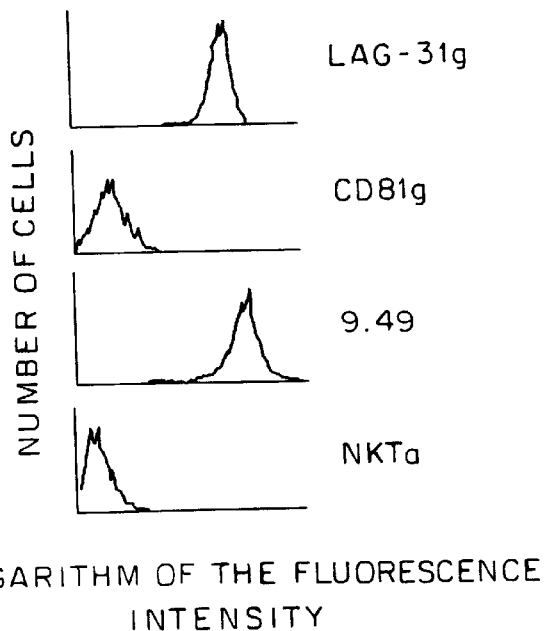
FIG. 11A–11C show the inhibition of clone T154 proliferation by crosslinked LAG-3 Ig.
Figure 11B:
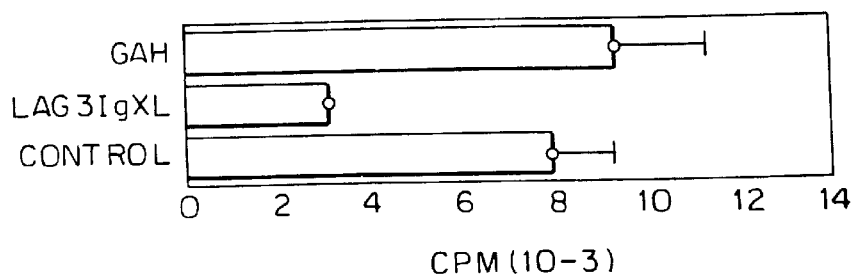

FIG. 11 depicts an experiment in which clone T154 has been preincubated with LAG-3Ig bound ("cross-linked") to a second reactant (polyclonal serum specific for the constant region of human immunoglobulins). The degree of binding of LAG-3Ig to the cells is measured by immunofluorescence (FIG. 11A). FIG. 11B shows that a more than 50% inhibition of the proliferation of clone T154 is produced by LAG-3Ig. Under the same experimental conditions, no effect is observed with the control CD8Ig or with LAG-3Ig without "cross-linking" (not shown in the figure).

Figure 11C:
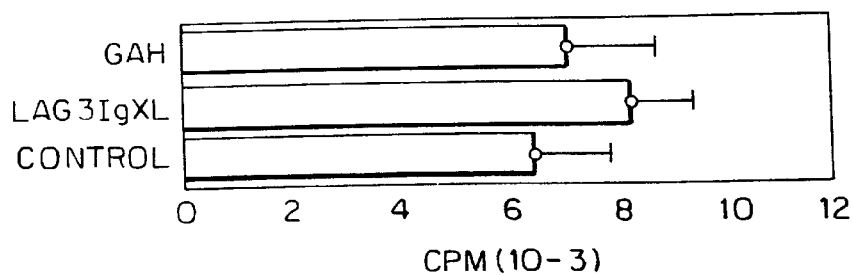

FIG. 11C also shows that no effect is observed when LAG-3Ig is used to bind ("cross-link") the MHC Class II molecules expressed by antigen-presenting B cells.

Figure 12:
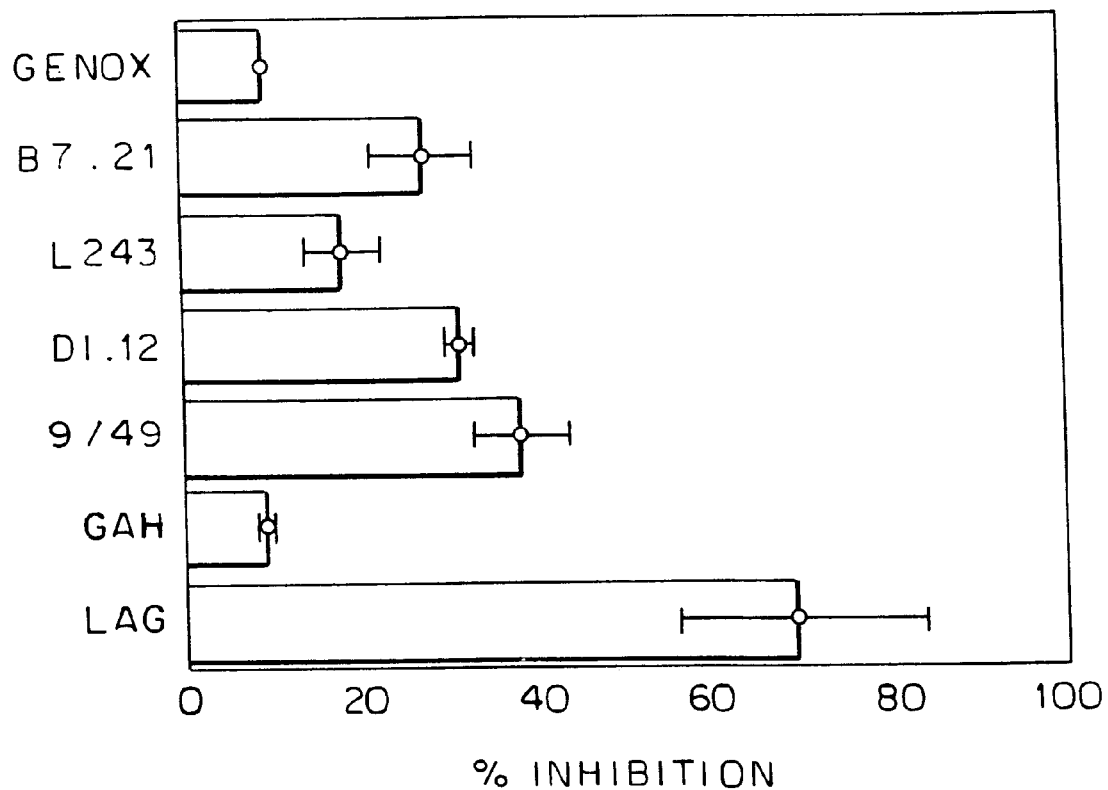
FIG. 12 compares inhibition of T cell proliferation by anti-Class II antibodies to inhibition of T cell proliferation by LAG-3 Ig.

The possible effects of bound ("cross-linked") anti-Class II monoclonal antibodies in relation to the proliferation of T cells were compared to those of LAG-3Ig. A weak inhibition (less than 50% is observed with antibody 949 and antibody D1.12 (anti-DR) bound to a goat anti-mouse polyclonal serum (FIG. 12). The inhibition of proliferation is hence epitope-dependent, the largest effect being obtained with the epitope of LAG-3 specific for the binding to Classes II.

The effects of LAG-3Ig on the proliferation of T cells were also studied using different signals on another CD$_4^+$ T clone, clone TDEL specific for peptide 34–53 of the basic myelin protein.

Figure 13A:
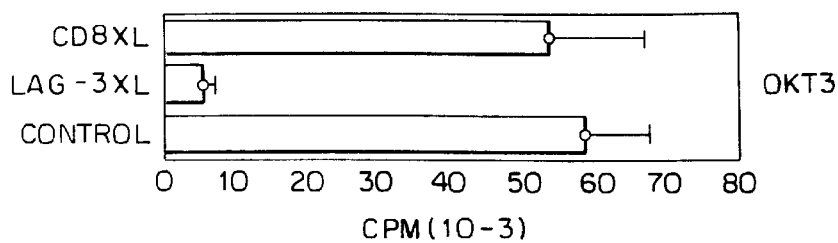
FIG. 13A–13D show that T cell proliferation in response to OKT3 (FIG. 13A), lectins (FIG. 13B), and low-concentration $IL_2$ (FIG. 13C) is inhibited by LAG-3 Ig but proliferation in response to high-concentration $IL_2$ is not inhibited by LAG-3 Ig (FIG. 13D).
Figure 13B:
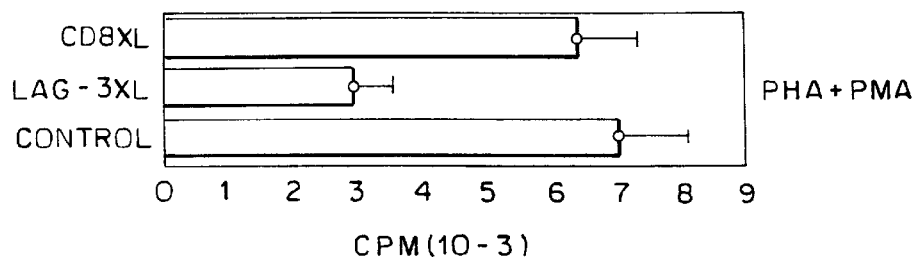
Figure 13C:
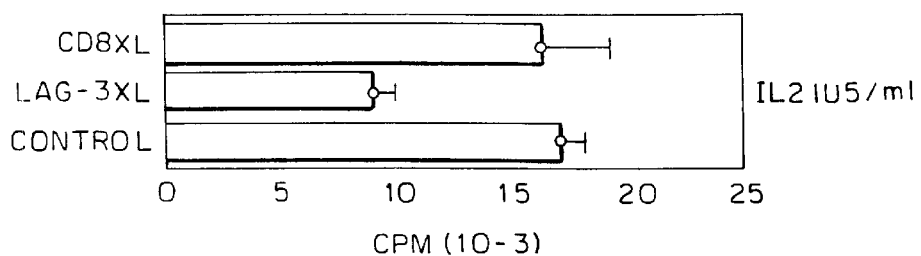
Figure 13D:
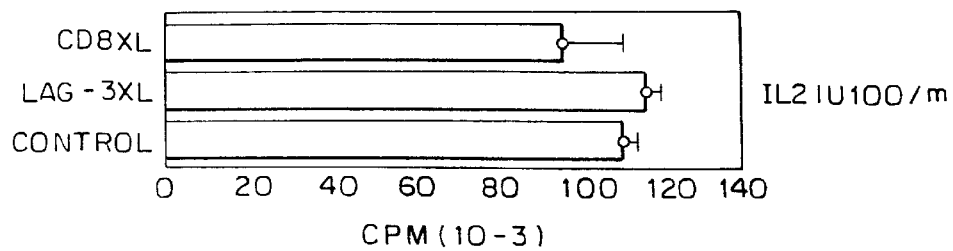

An inhibition of proliferation is observed (n=2) when TDEL is stimulated with the antigen (not shown), with immobilized OKT3 (FIG. 13A), with lectins (PHA+PMA) (FIG. 13B) and with 5 IU/ml of IL$_2$ (FIG. 13C). No inhibition is observed with 100 IU/ml of IL$_2$ (FIG. 13D).

In conclusion, these results collectively show that LAG-3 and MHC Class II molecules, which are each T cell-activating antigens, may be likened to effector molecules involved in the phase of inactivation of T cell responses. Moreover, these results illustrate the importance of interactions between T cells in the control of the cellular immune response.

EXAMPLE 7

Stimulation of cell cytotoxicity by LAG-3Ig

The role of LAG-3Ig in relation to cell cytotoxicity is studied on two types of effector cells:

freshly drawn human peripheral blood lymphocytes (PBL),

S1B5 line cells (clone of human NK cells).

The cytotoxic activity of these cells is measured by counting the $^{51}$Cr released into the medium by previously labelled target cells, in the presence or absence of LAG-3Ig in the medium.

Figure 14:
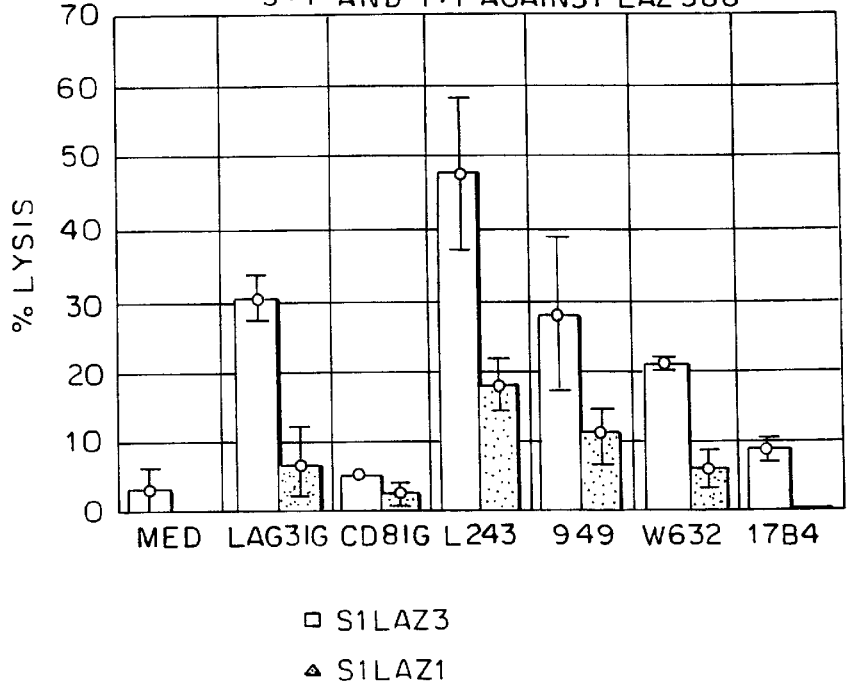
FIG. 14 shows clone S1B5 cytotoxicity towards Epstein-Barr virus transformed human B cells.

FIG. 14 shows the degree of cytotoxicity of S1B5 for a line of human B cells transformed by Epstein-Barr virus and carrying major histocompatibility complex Class I and II antigens (LAB 388 line), as a function of different reactants added to the cultures.

Measurements are carried out after 4 hours of coculture for effector/target (S1B5/LAZ 388) cell ratios of 3:1 (clear columns) of 1:1 (shaded columns).

The negative controls consist of medium alone (MED), the immunoadhesin CD8Ig and the monoclonal antibody 17.B4 (anti-LAG-3).

The positive controls consist of three different monoclonal antibodies:

antibody L243 directed against Class II DR antigens, antibody 9.49 directed against Class II DR, DP DQ antigens, antibody W632 directed against human major histocompatibility complex Class I antigens.

Anti-HLA Class I (W632) or Class II (L243) antibodies increase the lysis of the target cells (and not the 17B4 control). The immunoadhesin LAG-3Ig increases the lysis. The CD8Ig control has no effect.

Figure 15:
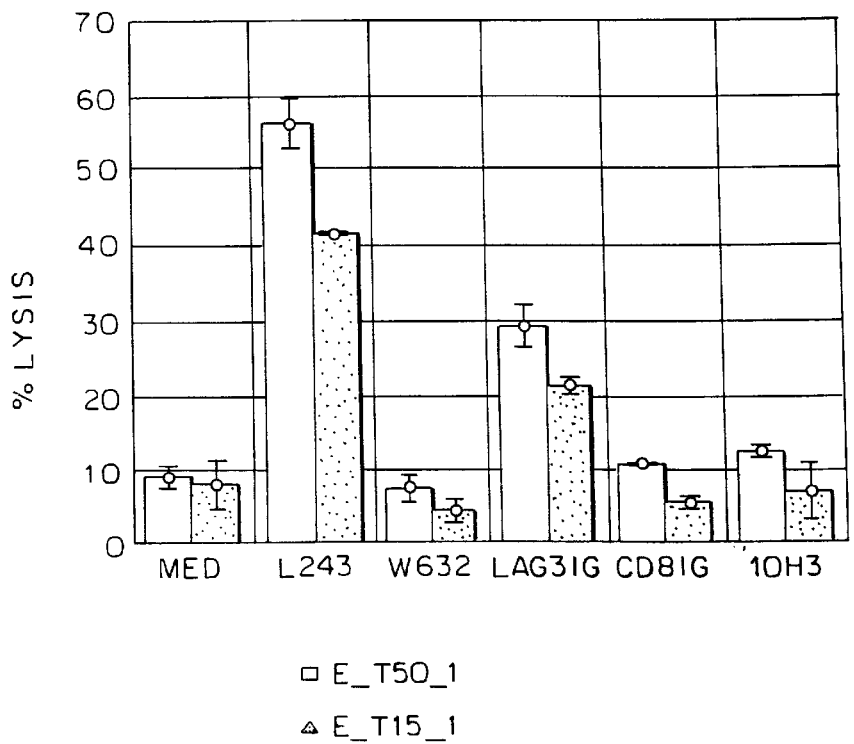
FIG. 15 shows peripheral blood lymphocyte cytotoxicity towards HLA Class I⁻ Daudi cells.

FIG. 15 shows the results of an experiment similar to the above, in which the cytotoxicity of PBL with respect to Daudi cells (HLA Class I) is measured, for effector/target ratios of 50:1 (clear columns) and 15:1 (shaded columns). The reactants added to the medium are the same as the ones used in the first experiment, except for antibody 9.49 and antibody 17.B4. Antibody 10H3 is an isotype IgG1 immunoglobulin specific for the CD45 surface antigen. It is used as negative control.

No change is observed with an antibody directed against major histocompatibility complex Class I antigens (W632).

The data from these two series of measurements show that, compared to negative controls, LAG-3Ig activates the cytotoxicity of NK cells. This effect is similar to the one observed antibodies directed against MHC Class II molecules.

BIBLIOGRAPHIC REFERENCES

1. TRIEBEL T. et al., 1990, J. Exp. Med. 171, 1393–1405

2. BAIXERAS E. et al., 1992, J. Exp. Med. 176, 327–337

3. COSGROVE D. et al., 1991, Cell 66, 1051–1066

4. RAHEMTULLA A. et al., 1991, Nature 353, 180–184

5. TRAUNECKER A. et al., 1988, Nature 331, 84–86

6. BENEDICT A. A. et al., 1967, Methods in Immunology 1, 197–306 (1967)

7. YELTON D. E. et al., Ann. Rev. of Biochem. 50, 657–680 (1981)

8. HUARD B. et al., Immunogenetics 39:213

9. MANIATIS T. et al. (1982), Molecular cloning: A laboratory manual—Cold Spring Harbor Laboratory, New-York.

10. SEED B., 1987, Nature 329, 840–842

11. COLE S. C. et al., Biotechnology 11, 1014–1024, 1993

12. COLE S. C. et al., Biotechnology 11, 1014–1024, 1993.

TABLE No. 1

| Atom name | x | y | z | residue name and no. | | atom type, charge and no. | |
|---|---|---|---|---|---|---|---|
| N | 25.172370911 | 27.259836197 | 67.855064392 | AP-n | 40 | n3 | −0.5000 | 1 |
| HN2 | 25.667764664 | 26.471963882 | 67.420585632 | AP-n | 40 | hn | 0.1300 | 2 |
| CA | 24.625223160 | 26.867494583 | 69.180244446 | AP-n | 40 | ca | 0.1200 | 3 |
| HN1 | 24.393711090 | 27.474891663 | 67.220008850 | AP-n | 40 | hn | 0.1300 | 4 |
| HA | 23.936895370 | 27.680395126 | 69.464080811 | AP-n | 40 | h | 0.0700 | 5 |
| C | 25.662780762 | 26.773513794 | 70.350120544 | AP-n | 40 | c' | 0.3800 | 6 |
| O | 25.295415878 | 27.090747833 | 71.482070923 | AP-n | 40 | o' | −0.4100 | 7 |
| CB | 23.766021729 | 25.587018967 | 68.990669250 | AP-n | 40 | c2 | −0.2600 | 8 |
| HB1 | 23.060285568 | 25.727443695 | 68.152351379 | AP-n | 40 | h | 0.0700 | 9 |
| HB2 | 24.413969040 | 24.744903564 | 68.686981201 | AP-n | 40 | h | 0.0700 | 10 |
| CG | 22.921775818 | 25.153419495 | 70.196960449 | AP-n | 40 | c− | 0.3400 | 11 |
| OD1 | 22.069602966 | 25.929233551 | 70.676017761 | AP-n | 40 | o− | −0.5700 | 12 |
| OD2 | 23.115716934 | 24.009321213 | 70.667663574 | AP-n | 40 | o− | −0.5700 | 13 |
| N | 26.906179428 | 26.304588318 | 70.124969482 | SER | 41 | n | −0.5000 | 14 |
| CA | 27.860145569 | 25.912786484 | 71.207519531 | SER | 41 | ca | 0.1200 | 15 |
| HN | 27.120641708 | 26.221813202 | 69.126319885 | SER | 41 | hn | 0.2800 | 16 |
| HA | 27.374551773 | 25.088045120 | 71.766326904 | SER | 41 | h | 0.1000 | 17 |
| C | 28.252065659 | 27.005065918 | 72.271789551 | SER | 41 | c' | 0.3800 | 18 |
| O | 27.987834930 | 28.200620651 | 72.115295410 | SER | 41 | o' | −0.3800 | 19 |
| CB | 29.093601227 | 25.298025131 | 70.494880676 | SER | 41 | c2 | −0.1700 | 20 |
| HB1 | 28.786190033 | 24.599395752 | 69.690521240 | SER | 41 | h | 0.1000 | 21 |
| HB2 | 29.691858292 | 26.092912674 | 70.004081726 | SER | 41 | h | 0.1000 | 22 |
| OG | 29.905221939 | 24.578149796 | 71.424118042 | SER | 41 | oh | −0.3800 | 23 |

TABLE No. 1-continued

| Atom name | x | y | z | residue name and no. | | atom type, charge and no. | |
|---|---|---|---|---|---|---|---|
| HG | 30.662555695 | 24.231645584 | 70.939277649 | SER | 41 | ho | 0.3500 | 24 |
| N | 28.857526779 | 26.558052063 | 73.387054443 | GLY | 42 | n | −0.5000 | 25 |
| CA | 29.199718475 | 27.440891266 | 74.535232544 | GLY | 42 | cg | 0.0200 | 26 |
| HN | 29.251720428 | 25.616510391 | 73.267890930 | GLY | 42 | hn | 0.2800 | 27 |
| HA1 | 28.520187378 | 28.312047958 | 74.591857910 | GLY | 42 | h | 0.1000 | 28 |
| HA2 | 28.983697891 | 26.890144348 | 75.468444824 | GLY | 42 | h | 0.1000 | 29 |
| C | 30.691051483 | 27.875793657 | 74.601707458 | GLY | 42 | c' | 0.3800 | 30 |
| O | 31.504199982 | 27.026502609 | 74.980445862 | GLY | 42 | o' | −0.3800 | 31 |
| N | 31.113182068 | 29.132183075 | 74.266487122 | PRO | 43 | n | −0.4200 | 32 |
| CA | 32.558349609 | 29.476200104 | 74.126792908 | PRO | 43 | ca | 0.0600 | 33 |
| HA | 33.096603394 | 28.605407715 | 73.708091736 | PRO | 43 | h | 0.1000 | 34 |
| CD | 30.214075089 | 30.174203873 | 73.722633362 | PRO | 43 | c2 | 0.0600 | 35 |
| HD1 | 29.467987061 | 30.516298294 | 74.466743469 | PRO | 43 | h | 0.1000 | 36 |
| HD2 | 29.664882660 | 29.799777985 | 72.838768005 | PRO | 43 | h | 0.1000 | 37 |
| C | 33.318023682 | 29.988374710 | 75.414916992 | PRO | 43 | c' | 0.3800 | 38 |
| O | 32.682361603 | 30.557033539 | 76.312332153 | PRO | 43 | o' | −0.3800 | 39 |
| CB | 32.483139038 | 30.574260712 | 73.043136597 | PRO | 43 | c2 | −0.2000 | 40 |
| HB1 | 33.350620270 | 31.263189316 | 73.049049377 | PRO | 43 | h | 0.1000 | 41 |
| HB2 | 32.463790894 | 30.110534568 | 72.036743164 | PRO | 43 | h | 0.1000 | 42 |
| CG | 31.160949707 | 31.299722672 | 73.307487488 | PRO | 43 | c2 | −0.2000 | 43 |
| HG1 | 31.279897690 | 32.024162292 | 74.137779236 | PRO | 43 | h | 0.1000 | 44 |
| HG2 | 30.794561386 | 31.862808228 | 72.428352356 | PRO | 43 | h | 0.1000 | 45 |
| N | 34.683673859 | 29.902477264 | 75.503486633 | PRO | 44 | n | −0.4200 | 46 |
| CA | 35.485736847 | 30.679145813 | 76.490524292 | PRO | 44 | ca | 0.0600 | 47 |
| HA | 35.018527985 | 30.645456314 | 77.491592407 | PRO | 44 | h | 0.1000 | 48 |
| CD | 35.509281158 | 29.014368057 | 74.655700684 | PRO | 44 | c2 | 0.0600 | 49 |
| HD1 | 35.411357880 | 29.247959137 | 73.577461243 | PRO | 44 | h | 0.1000 | 50 |
| HD2 | 35.214973450 | 27.955932617 | 74.801994324 | PRO | 44 | h | 0.1000 | 51 |
| C | 35.700843811 | 32.172924042 | 76.063224792 | PRO | 44 | c' | 0.3800 | 52 |
| O | 36.448230743 | 32.477428436 | 75.126922607 | PRO | 44 | o' | −0.3800 | 53 |
| CB | 36.779544830 | 29.842718124 | 76.547348022 | PRO | 44 | c2 | −0.2000 | 54 |
| HB1 | 37.662769318 | 30.430650711 | 76.863670349 | PRO | 44 | h | 0.1000 | 55 |
| HB2 | 36.667564392 | 29.027103424 | 77.288825989 | PRO | 44 | h | 0.1000 | 56 |
| CG | 36.940769196 | 29.250995636 | 75.143180847 | PRO | 44 | c2 | −0.2000 | 57 |
| HG1 | 37.446662903 | 29.982709886 | 74.483322144 | PRO | 44 | h | 0.1000 | 58 |
| HG2 | 37.553295135 | 28.329860687 | 75.134750366 | PRO | 44 | h | 0.1000 | 59 |
| N | 35.026676178 | 33.104183197 | 76.753837585 | ALA | 45 | n | −0.5000 | 60 |
| CA | 35.034278870 | 34.544979095 | 76.400695801 | ALA | 45 | ca | 0.1200 | 61 |
| HN | 34.452354431 | 32.747509003 | 77.536170959 | ALA | 45 | hn | 0.2800 | 62 |
| HA | 35.105010986 | 34.659946442 | 75.298950195 | ALA | 45 | h | 0.1000 | 63 |
| C | 36.209384918 | 35.322113037 | 77.076705933 | ALA | 45 | c' | 0.3800 | 64 |
| O | 36.163528442 | 35.637268066 | 78.268325806 | ALA | 45 | o' | −0.3800 | 65 |
| CB | 33.646369934 | 35.083190918 | 76.800727844 | ALA | 45 | c3 | −0.3000 | 66 |
| HB1 | 33.534698486 | 36.150661469 | 76.535202026 | ALA | 45 | h | 0.1000 | 67 |
| HB2 | 32.628392029 | 34.539138794 | 76.290328979 | ALA | 45 | h | 0.1000 | 68 |
| HB3 | 33.465579987 | 35.001335144 | 77.890525818 | ALA | 45 | h | 0.1000 | 69 |
| N | 37.266757965 | 35.613758087 | 76.297294617 | ALA | 46 | n | −0.5000 | 70 |
| HN | 37.216701508 | 35.231555939 | 75.346885681 | ALA | 46 | hn | 0.2800 | 71 |
| CA | 38.489383698 | 36.310386658 | 76.786270142 | ALA | 46 | ca | 0.1200 | 72 |
| HA | 38.262126923 | 36.871456146 | 77.716934204 | ALA | 46 | h | 0.1000 | 73 |
| C | 39.058414459 | 37.311935425 | 75.727844238 | ALA | 46 | c' | 0.3800 | 74 |
| O | 38.922710419 | 37.100418091 | 74.516731262 | ALA | 46 | o' | −0.3800 | 75 |
| CB | 39.526046753 | 35.215301514 | 77.108406067 | ALA | 46 | c3 | −0.3000 | 76 |
| HB1 | 40.446556091 | 35.633434296 | 77.555480957 | ALA | 46 | h | 0.1000 | 77 |
| HB2 | 39.131206512 | 34.469978333 | 77.822120667 | ALA | 46 | h | 0.1000 | 78 |
| HB3 | 39.821903229 | 34.663463593 | 76.197715759 | ALA | 46 | h | 0.1000 | 79 |
| N | 39.737388611 | 38.384365082 | 76.180320740 | ALA | 47 | n | −0.5000 | 80 |
| CA | 40.295833588 | 39.429889679 | 75.275863647 | ALA | 47 | ca | 0.1200 | 81 |
| HN | 39.717037201 | 38.512592316 | 77.196357727 | ALA | 47 | hn | 0.2800 | 82 |
| HA | 39.901103973 | 39.319335938 | 74.245994568 | ALA | 47 | h | 0.1000 | 83 |
| C | 41.869789124 | 39.413467407 | 75.170806885 | ALA | 47 | c' | 0.3800 | 84 |
| O | 42.518333435 | 40.166862488 | 75.906578064 | ALA | 47 | o' | −0.3800 | 85 |
| CB | 39.722030640 | 40.769996643 | 75.786285400 | ALA | 47 | c3 | −0.3000 | 86 |
| HB1 | 40.045078278 | 41.611721039 | 75.145561218 | ALA | 47 | h | 0.1000 | 87 |
| HB2 | 38.615306854 | 40.778987885 | 75.787467957 | ALA | 47 | h | 0.1000 | 88 |
| HB3 | 40.059757233 | 41.007873535 | 76.813346863 | ALA | 47 | h | 0.1000 | 89 |
| N | 42.537422180 | 38.621597290 | 74.274406433 | PRO | 48 | n | −0.4200 | 90 |
| CA | 44.009857178 | 38.718185425 | 74.045745850 | PRO | 48 | ca | 0.0600 | 91 |
| HA | 44.539390564 | 38.855972290 | 75.008773804 | PRO | 48 | h | 0.1000 | 92 |
| CD | 41.903011322 | 37.522361755 | 73.516281128 | PRO | 48 | c2 | 0.0600 | 93 |
| HD1 | 41.081176758 | 37.871139526 | 72.860626221 | PRO | 48 | h | 0.1000 | 94 |
| HD2 | 41.490711212 | 36.761222839 | 74.206848145 | PRO | 48 | h | 0.1000 | 95 |
| C | 44.448692322 | 39.844142914 | 73.044319153 | PRO | 48 | c' | 0.3800 | 96 |
| O | 43.693031311 | 40.225761414 | 72.144134521 | PRO | 48 | o' | −0.3800 | 97 |
| CB | 44.301902771 | 37.304885864 | 73.500595093 | PRO | 48 | c2 | −0.2000 | 98 |

TABLE No. 1-continued

| Atom name | x | y | z | residue name and no. | | atom type, charge and no. | | |
|---|---|---|---|---|---|---|---|---|
| HB1 | 45.227554321 | 37.245040894 | 72.897834778 | PRO | 48 | h | 0.1000 | 99 |
| HB2 | 44.442562103 | 36.597515106 | 74.341529846 | PRO | 48 | h | 0.1000 | 100 |
| CG | 43.051033020 | 36.925685883 | 72.702011108 | PRO | 48 | c2 | -0.2000 | 101 |
| HG1 | 43.084365845 | 37.389282227 | 71.696128845 | PRO | 48 | h | 0.1000 | 102 |
| HG2 | 42.948661804 | 35.835418701 | 72.555740356 | PRO | 48 | h | 0.1000 | 103 |
| N | 45.700798035 | 40.324272156 | 73.165817261 | GLY | 49 | n | -0.5000 | 104 |
| CA | 46.289730072 | 41.291931152 | 72.184875488 | GLY | 49 | og | 0.0200 | 105 |
| HN | 46.207077026 | 39.986907959 | 73.991729736 | GLY | 49 | hn | 0.2800 | 106 |
| HA1 | 45.620616913 | 41.460151672 | 71.317451477 | GLY | 49 | h | 0.1000 | 107 |
| HA2 | 46.357063293 | 42.283206940 | 72.672386169 | GLY | 49 | h | 0.1000 | 108 |
| C | 47.682319641 | 40.950855255 | 71.600997925 | GLY | 49 | c' | 0.3800 | 109 |
| O | 48.560806274 | 41.811416626 | 71.601501465 | GLY | 49 | o' | -0.3800 | 110 |
| N | 47.842975616 | 39.718383789 | 71.091018677 | HIS | 50 | n | -0.5000 | 111 |
| HN | 46.947166443 | 39.222202301 | 71.052452087 | HIS | 50 | hn | 0.2800 | 112 |
| CA | 49.020114899 | 39.216835022 | 70.306198120 | HIS | 50 | ca | 0.1200 | 113 |
| HA | 49.324539185 | 38.296161652 | 70.836235046 | HIS | 50 | h | 0.1000 | 114 |
| C | 50.400863647 | 39.993576050 | 70.182189941 | HIS | 50 | c' | 0.3800 | 115 |
| O | 50.733478546 | 40.446022034 | 69.081466675 | HIS | 50 | o' | -0.3800 | 116 |
| CB | 48.455345154 | 38.673969269 | 68.953773499 | HIS | 50 | c2 | -0.2000 | 117 |
| HB1 | 49.238502502 | 38.051708221 | 68.481765747 | HIS | 50 | h | 0.1000 | 118 |
| HB2 | 47.639427185 | 37.951225281 | 69.144165039 | HIS | 50 | h | 0.1000 | 119 |
| CG | 47.954322815 | 39.695293427 | 67.919425964 | HIS | 50 | c5 | 0.1000 | 120 |
| ND1 | 46.759342194 | 40.404747009 | 68.035293579 | HIS | 50 | np | -0.4200 | 121 |
| CE1 | 46.825572968 | 41.133701324 | 66.873245239 | HIS | 50 | c5 | 0.2700 | 122 |
| NE2 | 47.887611389 | 40.964004517 | 66.014495850 | HIS | 50 | np | -0.5000 | 123 |
| CD2 | 48.617565155 | 40.019775391 | 66.717041016 | HIS | 50 | c5 | 0.0100 | 124 |
| HE1 | 46.043247223 | 41.852840424 | 66.655242920 | HIS | 50 | h | 0.1300 | 125 |
| HE2 | 48.092224121 | 41.403381348 | 65.108955383 | HIS | 50 | hn | 0.2800 | 126 |
| HD2 | 49.566501617 | 39.599807739 | 66.396347046 | HIS | 50 | h | 0.1300 | 127 |
| N | 51.278770447 | 40.105480194 | 71.226615906 | PRO | 51 | n | -0.4200 | 128 |
| CA | 52.667034149 | 40.618915558 | 71.077911377 | PRO | 51 | ca | 0.0600 | 129 |
| HA | 52.723186493 | 41.393623352 | 70.287094116 | PRO | 51 | h | 0.1000 | 130 |
| CD | 50.956447601 | 39.767082214 | 72.624496460 | PRO | 51 | c2 | 0.0600 | 131 |
| HD1 | 50.920970917 | 38.670558929 | 72.747383118 | PRO | 51 | h | 0.1000 | 132 |
| HD2 | 49.988422394 | 40.190521240 | 72.947166443 | PRO | 51 | h | 0.1000 | 133 |
| C | 53.707103729 | 39.478122711 | 70.804489136 | PRO | 51 | c' | 0.3800 | 134 |
| O | 53.623699188 | 38.391666412 | 71.391418457 | PRO | 51 | o' | -0.3800 | 135 |
| CB | 52.846694946 | 41.283794403 | 72.455955505 | PRO | 51 | c2 | -0.2000 | 136 |
| HB1 | 53.907955170 | 41.442169189 | 72.729286194 | PRO | 51 | h | 0.1000 | 137 |
| HB2 | 52.373264313 | 42.285846710 | 72.449127197 | PRO | 51 | h | 0.1000 | 138 |
| CG | 52.105823517 | 40.370025635 | 73.440399170 | PRO | 51 | c2 | -0.2000 | 139 |
| HG1 | 52.782051086 | 39.565395355 | 73.789718628 | PRO | 51 | h | 0.1000 | 140 |
| HG2 | 51.753723145 | 40.912036896 | 74.337333679 | PRO | 51 | h | 0.1000 | 141 |
| N | 54.704883575 | 39.729522705 | 69.933471680 | LEU | 52 | n | -0.5000 | 142 |
| CA | 55.791530609 | 38.746330261 | 69.603820801 | LEU | 52 | ca | 0.1200 | 143 |
| HN | 54.653743744 | 40.652229309 | 69.490356445 | LEU | 52 | hn | 0.2800 | 144 |
| HA | 56.479202271 | 39.288208008 | 68.927917480 | LEU | 52 | h | 0.1000 | 145 |
| C | 55.301837921 | 37.525024414 | 68.745040894 | LEU | 52 | c' | 0.3800 | 146 |
| O | 55.637695313 | 37.425930023 | 67.562049866 | LEU | 52 | o' | -0.3800 | 147 |
| CB | 56.671585083 | 38.316761017 | 70.829437256 | LEU | 52 | c2 | -0.2000 | 148 |
| HB1 | 56.036743164 | 37.710464478 | 71.502593994 | LEU | 52 | h | 0.1000 | 149 |
| HB2 | 57.445541382 | 37.602729797 | 70.487434387 | LEU | 52 | h | 0.1000 | 150 |
| CG | 57.363307953 | 39.420749664 | 71.675102234 | LEU | 52 | c1 | -0.1000 | 151 |
| HG | 56.617557526 | 40.200679779 | 71.926834106 | LEU | 52 | h | 0.1000 | 152 |
| CD1 | 57.875057220 | 38.833915710 | 73.004547119 | LEU | 52 | c3 | -0.3000 | 153 |
| HD11 | 58.353130341 | 39.601875305 | 73.642135620 | LEU | 52 | h | 0.1000 | 154 |
| HD12 | 57.048751831 | 38.403957367 | 73.601577759 | LEU | 52 | h | 0.1000 | 155 |
| HD13 | 58.618564606 | 38.028480530 | 72.852462769 | LEU | 52 | h | 0.1000 | 156 |
| CD2 | 58.531608582 | 40.085853577 | 70.927200317 | LEU | 52 | c3 | -0.3000 | 157 |
| HD21 | 59.028976440 | 40.857166290 | 71.545303345 | LEU | 52 | h | 0.1000 | 158 |
| HD22 | 59.309509277 | 39.355545044 | 70.634819031 | LEU | 52 | h | 0.1000 | 159 |
| HD23 | 58.192760468 | 40.592193604 | 70.005569458 | LEU | 52 | h | 0.1000 | 160 |
| N | 54.534648895 | 36.601863861 | 69.354270935 | ALA | 53 | n | -0.5000 | 161 |
| CA | 53.940563202 | 35.420303345 | 68.673507690 | ALA | 53 | ca | 0.1200 | 162 |
| HN | 54.159572601 | 36.958141327 | 70.246543884 | ALA | 53 | hn | 0.2800 | 163 |
| HA | 53.600482941 | 35.753322601 | 67.671340942 | ALA | 53 | h | 0.1000 | 164 |
| C | 52.639778137 | 34.883575439 | 69.383995056 | ALA | 53 | c' | 0.3800 | 165 |
| O | 51.628326416 | 34.818698883 | 68.677047729 | ALA | 53 | o' | -0.3800 | 166 |
| CB | 55.008785248 | 34.330768585 | 68.423698425 | ALA | 53 | c3 | -0.3000 | 167 |
| HB1 | 54.582756042 | 33.460170746 | 67.892036438 | ALA | 53 | h | 0.1000 | 168 |
| HB2 | 55.828662872 | 34.711517334 | 67.787384851 | ALA | 53 | h | 0.1000 | 169 |
| HB3 | 55.479701996 | 33.961406708 | 69.351325989 | ALA | 53 | h | 0.1000 | 170 |
| N | 52.555103302 | 34.484893799 | 70.698265076 | PRO | 54 | n | -0.4200 | 171 |
| CA | 51.304950714 | 33.917499542 | 71.286506653 | PRO | 54 | ca | 0.0600 | 172 |
| HA | 50.878768921 | 33.172523499 | 70.584587097 | PRO | 54 | h | 0.1000 | 173 |

TABLE No. 1-continued

| Atom name | x | y | z | residue name and no. | | atom type, charge and no. | | |
|---|---|---|---|---|---|---|---|---|
| CD | 53.705833435 | 34.435420990 | 71.626182556 | PRO | 54 | c2 | 0.0600 | 174 |
| HD1 | 54.215991974 | 35.409980774 | 71.739936829 | PRO | 54 | h | 0.1000 | 175 |
| HD2 | 54.453365326 | 33.693523407 | 71.288909912 | PRO | 54 | h | 0.1000 | 176 |
| C | 50.177021027 | 34.945980072 | 71.642837524 | PRO | 54 | c' | 0.3800 | 177 |
| O | 50.377983093 | 36.164409637 | 71.677795410 | PRO | 54 | o' | −0.3800 | 178 |
| CB | 51.867893219 | 33.173828125 | 72.519187927 | PRO | 54 | c2 | −0.2000 | 179 |
| HB1 | 51.135505676 | 33.051830292 | 73.340660095 | PRO | 54 | h | 0.1000 | 180 |
| HB2 | 52.181377411 | 32.150829315 | 72.232276917 | PRO | 54 | h | 0.1000 | 181 |
| CG | 53.087123871 | 33.989192963 | 72.949317932 | PRO | 54 | c2 | −0.2000 | 182 |
| HG1 | 52.768703461 | 34.871643066 | 73.538475037 | PRO | 54 | h | 0.1000 | 183 |
| HG2 | 53.791828156 | 33.414070129 | 73.579086304 | PRO | 54 | h | 0.1000 | 184 |
| N | 48.977436066 | 34.414421082 | 71.936706543 | GLY | 55 | n | −0.5000 | 185 |
| CA | 47.822620392 | 35.225021362 | 72.404747009 | GLY | 55 | cg | 0.0200 | 186 |
| HN | 48.958133698 | 33.389709473 | 71.929512024 | GLY | 55 | hn | 0.2800 | 187 |
| HA1 | 47.830284119 | 36.238574982 | 71.963676453 | GLY | 55 | h | 0.1000 | 188 |
| HA2 | 46.896526337 | 34.772380829 | 72.004432678 | GLY | 55 | h | 0.1000 | 189 |
| C | 47.670829773 | 35.263648987 | 73.950416565 | GLY | 55 | c' | 0.3800 | 190 |
| O | 47.247509003 | 34.242198944 | 74.498336792 | GLY | 55 | o' | −0.3800 | 191 |
| N | 47.956153870 | 36.372848511 | 74.696281433 | PRO | 56 | n | −0.4200‘ | 192 |
| CA | 47.830066681 | 36.396587372 | 76.179130554 | PRO | 56 | ca | 0.0600 | 193 |
| HA | 48.225147247 | 35.457695007 | 76.619560242 | PRO | 56 | h | 0.1000 | 194 |
| CD | 48.653686523 | 37.556163788 | 74.163940430 | PRO | 56 | c2 | 0.0600 | 195 |
| HD1 | 48.108860016 | 38.040233612 | 73.332565308 | PRO | 56 | h | 0.1000 | 196 |
| HD2 | 49.652721405 | 37.256084442 | 73.799308777 | PRO | 56 | h | 0.1000 | 197 |
| C | 46.361907959 | 36.604877472 | 76.668052673 | PRO | 56 | c' | 0.3800 | 198 |
| O | 45.890090942 | 37.732730865 | 76.845039368 | PRO | 56 | o' | −0.3800 | 199 |
| CB | 48.804897308 | 37.531764984 | 76.560951233 | PRO | 56 | c2 | −0.2000 | 200 |
| HB1 | 48.542221069 | 38.034294128 | 77.511970520 | PRO | 56 | h | 0.1000 | 201 |
| HB2 | 49.825592041 | 37.124542236 | 76.697402954 | PRO | 56 | h | 0.1000 | 202 |
| CG | 48.782566071 | 38.488700867 | 75.368530273 | PRO | 56 | c2 | −0.2000 | 203 |
| HG1 | 47.903289795 | 39.158111572 | 75.434867859 | PRO | 56 | h | 0.1000 | 204 |
| HG2 | 49.679012299 | 39.133480072 | 75.321792603 | PRO | 56 | h | 0.1000 | 205 |
| N | 45.650573730 | 35.488880157 | 76.896896362 | HIS | 57 | n | −0.5000 | 206 |
| HN | 46.046119690 | 34.657379150 | 76.439048767 | HIS | 57 | hn | 0.2800 | 207 |
| CA | 44.244419098 | 35.504474640 | 77.387596130 | HIS | 57 | ca | 0.1200 | 208 |
| HA | 43.667560577 | 36.207649231 | 76.759368896 | HIS | 57 | h | 0.1000 | 209 |
| C | 44.173530579 | 35.943927765 | 78.901000977 | HIS | 57 | c' | 0.3800 | 210 |
| O | 44.750030518 | 35.234142303 | 79.736030579 | HIS | 57 | o' | −0.3800 | 211 |
| CB | 43.610416412 | 34.095542908 | 77.185058594 | HIS | 57 | c2 | −0.2000 | 212 |
| HB1 | 44.270858765 | 33.323795319 | 77.623748779 | HIS | 57 | h | 0.1000 | 213 |
| HB2 | 42.689029694 | 34.034877777 | 77.796188354 | HIS | 57 | h | 0.1000 | 214 |
| CG | 43.250400543 | 33.671833038 | 75.751731873 | HIS | 57 | c5 | 0.1000 | 215 |
| ND1 | 44.116428375 | 33.723644257 | 74.666069031 | HIS | 57 | np | −0.4200 | 216 |
| CE1 | 43.325973511 | 33.139041901 | 73.713264465 | HIS | 57 | c5 | 0.2700 | 217 |
| NE2 | 42.066158295 | 32.716590881 | 74.036811829 | HIS | 57 | np | −0.5000 | 218 |
| CD2 | 42.045005798 | 33.048488617 | 75.379264832 | HIS | 57 | c5 | 0.0100 | 219 |
| HE1 | 43.712070465 | 33.001682281 | 72.711807251 | HIS | 57 | h | 0.1300 | 220 |
| HE2 | 41.370864868 | 32.225383759 | 73.464263916 | HIS | 57 | hn | 0.2800 | 221 |
| HD2 | 41.236827850 | 32.815635681 | 76.058380127 | HIS | 57 | h | 0.1300 | 222 |
| N | 43.513858795 | 37.068405151 | 79.318038940 | PRO | 58 | n | −0.4200 | 223 |
| CA | 43.593978882 | 37.569736481 | 80.719970703 | PRO | 58 | ca | 0.0600 | 224 |
| HA | 44.657642365 | 37.630668640 | 81.026939392 | PRO | 58 | h | 0.1000 | 225 |
| CD | 42.833599091 | 38.010932922 | 78.407653809 | PRO | 58 | c2 | 0.0600 | 226 |
| HD1 | 42.093353271 | 37.516807556 | 77.751007080 | PRO | 58 | h | 0.1000 | 227 |
| HD2 | 43.569110870 | 38.527889252 | 77.758674622 | PRO | 58 | h | 0.1000 | 228 |
| C | 42.805988312 | 36.695770264 | 81.747009277 | PRO | 58 | c' | 0.3800 | 229 |
| O | 41.569808960 | 36.693984985 | 81.769706726 | PRO | 58 | o' | −0.3800 | 230 |
| CB | 43.072513580 | 39.016571045 | 80.579101563 | PRO | 58 | c2 | −0.2000 | 231 |
| HB1 | 42.559799194 | 39.392253876 | 81.485702515 | PRO | 58 | h | 0.1000 | 232 |
| HB2 | 43.920654297 | 39.706352234 | 80.398040771 | PRO | 58 | h | 0.1000 | 233 |
| CG | 42.156440735 | 38.999496460 | 79.353309631 | PRO | 58 | c2 | −0.2000 | 234 |
| HG1 | 41.151851654 | 38.629653931 | 79.634307861 | PRO | 58 | h | 0.1000 | 235 |
| HG2 | 42.023620605 | 39.998752594 | 78.896965027 | PRO | 58 | h | 0.1000 | 236 |
| N | 43.540618896 | 35.961261749 | 82.605430603 | ALA | 59 | n | −0.5000 | 237 |
| HN | 44.537330627 | 35.932937622 | 82.365699768 | ALA | 59 | hn | 0.2800 | 238 |
| CA | 42.949653625 | 34.946206954 | 83.526855469 | ALA | 59 | ca | 0.1200 | 239 |
| HA | 42.197692871 | 34.355514526 | 82.965911865 | ALA | 59 | h | 0.1000 | 240 |
| C | 42.208984375 | 35.488863972 | 84.803985596 | ALA | 59 | c' | 0.3800 | 241 |
| O | 42.496433258 | 35.127353668 | 85.948333740 | ALA | 59 | o' | −0.3800 | 242 |
| CB | 44.107444763 | 33.975612640 | 83.839767456 | ALA | 59 | c3 | −0.3000 | 243 |
| HB1 | 43.761249542 | 33.130538940 | 84.463287354 | ALA | 59 | h | 0.1000 | 244 |
| HB2 | 44.544620514 | 33.531585693 | 82.924507141 | ALA | 59 | h | 0.1000 | 245 |
| HB3 | 44.925910950 | 34.467308044 | 84.399597168 | ALA | 59 | h | 0.1000 | 246 |
| N | 41.192062378 | 36.323741913 | 84.559051514 | ALA | 60 | n | −0.5000 | 247 |
| HN | 41.124549866 | 36.554912676 | 83.555343628 | ALA | 60 | hn | 0.2800 | 248 |

TABLE No. 1-continued

| Atom name | x | y | z | residue name and no. | | atom type, charge and no. | | |
|---|---|---|---|---|---|---|---|---|
| CA | 40.203086853 | 36.790748596 | 85.562988281 | ALA | 60 | ca | 0.1200 | 249 |
| HA | 40.023948669 | 35.965785980 | 86.283721924 | ALA | 60 | h | 0.1000 | 250 |
| C | 38.823528290 | 37.027305603 | 84.846977234 | ALA | 60 | c' | 0.3800 | 251 |
| O | 37.897804260 | 36.283885956 | 85.186340332 | ALA | 60 | o' | −0.3800 | 252 |
| CB | 40.756233215 | 37.971691132 | 86.389617920 | ALA | 60 | c3 | −0.3000 | 253 |
| HB1 | 40.004146576 | 38.357006073 | 87.102043152 | ALA | 60 | h | 0.1000 | 254 |
| HB2 | 41.631908417 | 37.656120300 | 86.987319946 | ALA | 60 | h | 0.1000 | 255 |
| HB3 | 41.090072632 | 38.818138123 | 85.765472412 | ALA | 60 | h | 0.1000 | 256 |
| N | 38.616340637 | 37.921970367 | 83.823921204 | PRO | 61 | n | −0.4200 | 257 |
| CA | 37.403762817 | 37.874496460 | 82.948486328 | PRO | 61 | ca | 0.0600 | 258 |
| HA | 36.491020203 | 37.824863434 | 83.573593140 | PRO | 61 | h | 0.1000 | 259 |
| CD | 39.556003571 | 39.003845215 | 83.459777832 | PRO | 61 | c2 | 0.0600 | 260 |
| HD1 | 40.594814301 | 38.658184052 | 83.304046631 | PRO | 61 | h | 0.1000 | 261 |
| HD2 | 39.571029663 | 39.778694153 | 84.250648499 | PRO | 61 | h | 0.1000 | 262 |
| C | 37.275394440 | 36.712963104 | 81.892074585 | PRO | 61 | c' | 0.3800 | 263 |
| O | 36.266387939 | 36.670307159 | 81.183494568 | PRO | 61 | o' | −0.3800 | 264 |
| CB | 37.473857880 | 39.266963959 | 82.286987305 | PRO | 61 | c2 | −0.2000 | 265 |
| HB1 | 36.949714661 | 39.321308136 | 81.312759399 | PRO | 61 | h | 0.1000 | 266 |
| HB2 | 36.985511780 | 40.017913818 | 82.938987732 | PRO | 61 | h | 0.1000 | 267 |
| CG | 38.968631744 | 39.571613312 | 82.168632507 | PRO | 61 | c2 | −0.2000 | 268 |
| HG1 | 39.397396088 | 39.046298981 | 81.292793274 | PRO | 61 | h | 0.1000 | 269 |
| HG2 | 39.180202484 | 40.649600983 | 82.039207458 | PRO | 61 | h | 0.1000 | 270 |
| N | 38.242324829 | 35.777751923 | 81.785034180 | SER | 62 | n | −0.5000 | 271 |
| CA | 38.186004639 | 34.624855042 | 80.844123840 | SER | 62 | ca | 0.1200 | 272 |
| HN | 39.035541534 | 35.927360535 | 82.416992188 | SER | 62 | hn | 0.2800 | 273 |
| HA | 37.921787262 | 35.006183624 | 79.841125488 | SER | 62 | h | 0.1000 | 274 |
| C | 37.145660400 | 33.532897949 | 81.261909485 | SER | 62 | c' | 0.3800 | 275 |
| O | 37.466091156 | 32.626064301 | 82.041137695 | SER | 62 | c' | −0.3800 | 276 |
| CB | 39.620265961 | 34.048240662 | 80.725196838 | SER | 62 | c2 | −0.1700 | 277 |
| HB1 | 39.660293579 | 33.306644440 | 79.904281616 | SER | 62 | h | 0.1000 | 278 |
| HB2 | 40.349685669 | 34.832687378 | 88.442802429 | SER | 62 | h | 0.1000 | 279 |
| OG | 40.032703400 | 33.414188385 | 81.938880920 | SER | 62 | oh | −0.3800 | 280 |
| HG | 39.252223969 | 32.931293488 | 82.256263733 | SER | 62 | ho | 0.3500 | 281 |
| N | 35.902244568 | 33.647918701 | 80.764541626 | SER | 63 | n | −0.5000 | 282 |
| CA | 34.747528076 | 32.874465942 | 81.297317505 | SER | 63 | ca | 0.1200 | 283 |
| HN | 35.768447876 | 34.503852844 | 80.205200195 | SER | 63 | hn | 0.2800 | 284 |
| HA | 35.064254761 | 32.265518188 | 82.170570374 | SER | 63 | h | 0.1000 | 215 |
| C | 34.106758118 | 31.936998367 | 80.231674194 | SER | 63 | c' | 0.3800 | 286 |
| O | 33.716896057 | 32.367130280 | 79.142120361 | SER | 63 | o' | −0.3800 | 287 |
| CB | 33.716815948 | 33.889484406 | 81.843544006 | SER | 63 | c2 | −0.1700 | 288 |
| HB1 | 34.199871063 | 34.571384430 | 82.572105408 | SER | 63 | h | 0.1000 | 289 |
| HB2 | 33.328830719 | 34.543502808 | 81.036796570 | SER | 63 | h | 0.1000 | 290 |
| OG | 32.634590149 | 33.222091675 | 82.496467590 | SER | 63 | oh | −0.3800 | 291 |
| HG | 32.159793854 | 32.710407257 | 81.832328796 | SER | 63 | ho | 0.3500 | 292 |
| N | 33.914913177 | 30.658897400 | 80.588378906 | TRP | 64 | n | −0.5000 | 293 |
| CA | 33.112319946 | 29.694124222 | 79.783546448 | TRP | 64 | ca | 0.1200 | 294 |
| HN | 34.221500397 | 30.422899246 | 81.538955688 | TRP | 64 | hn | 0.2800 | 295 |
| HA | 33.404731750 | 29.812168121 | 78.721931458 | TRP | 64 | h | 0.1000 | 296 |
| C | 31.573041916 | 29.961977005 | 79.883049011 | TRP | 64 | c' | 0.3800 | 297 |
| O | 30.996980667 | 29.940891266 | 80.975959778 | TRP | 64 | o' | −0.3800 | 298 |
| CB | 33.525466919 | 28.235471725 | 80.142707825 | TRP | 64 | c2 | −0.2000 | 299 |
| HB1 | 32.950366974 | 27.534402847 | 79.508041382 | TRP | 64 | h | 0.1000 | 300 |
| HB2 | 34.571674347 | 28.078489304 | 79.816658020 | TRP | 64 | h | 0.1000 | 301 |
| CG | 33.405326843 | 27.783784866 | 81.611763000 | TRP | 64 | c5 | 0.0000 | 302 |
| CD1 | 32.267101288 | 27.214570999 | 82.221214294 | TRP | 64 | c5 | 0.0100 | 303 |
| NE1 | 32.481933594 | 26.953943253 | 83.590408325 | TRP | 64 | np | −0.5000 | 304 |
| CE2 | 33.781982422 | 27.378627777 | 83.812339783 | TRP | 64 | c5 | 0.1100 | 305 |
| CD2 | 34.355152130 | 27.881061554 | 82.617965698 | TRP | 64 | c5 | 0.0000 | 306 |
| HD1 | 31.332025528 | 27.036033630 | 81.708480835 | TRP | 64 | h | 0.1000 | 307 |
| HE1 | 31.820940018 | 26.578481674 | 84.279945374 | TRP | 64 | hn | 0.2800 | 308 |
| CE3 | 35.681034088 | 28.394184113 | 82.615905762 | TRP | 64 | cp | −0.1000 | 309 |
| HE3 | 36.128986359 | 28.784986496 | 81.714393616 | TRP | 64 | h | 0.1000 | 310 |
| CZ3 | 36.396430969 | 28.387191772 | 83.815704346 | TRP | 64 | cp | −0.1000 | 311 |
| HZ3 | 37.405311584 | 28.776082993 | 83.832160950 | TRP | 64 | h | 0.1000 | 312 |
| CH2 | 35.830604553 | 27.888952255 | 84.994010925 | TRP | 64 | cp | −0.1000* | 313 |
| HH2 | 36.410472870 | 27.896844864 | 85.906951904 | TRP | 64 | h | 0.1000 | 314 |
| CZ2 | 34.527233124 | 27.382776260 | 85.014289856 | TRP | 64 | cp | −0.1000 | 315 |
| HZ2 | 34.097515106 | 27.006088257 | 85.929389954 | TRP | 64 | h | 0.1000 | 316 |
| N | 30.921329498 | 30.232547760 | 78.740600586 | GLY | 65 | n | −0.5000 | 317 |
| CA | 29.460748672 | 30.504768372 | 78.692192078 | GLY | 65 | cg | 0.0200 | 318 |
| HN | 31.520374298 | 30.302478790 | 77.901519775 | GLY | 65 | hn | 0.2800 | 319 |
| HA1 | 29.073087692 | 30.896234512 | 79.650825500 | GLY | 65 | h | 0.1000 | 320 |
| HA2 | 29.288171768 | 31.333106995 | 77.981094360 | GLY | 65 | h | 0.1000 | 321 |
| C | 28.633579254 | 29.293350220 | 78.197364807 | GLY | 65 | c' | 0.3800 | 322 |
| O | 28.566907883 | 29.137302399 | 76.975486755 | GLY | 65 | o' | −0.3800 | 323 |

TABLE No. 1-continued

| Atom name | x | y | z | residue name and no. | | atom type, charge and no. | |
|---|---|---|---|---|---|---|---|
| N | 27.989013672 | 28.429246902 | 79.038352966 | PRO | 66 | n | -0.4200 | 324 |
| CA | 27.282257080 | 27.212890625 | 78.546752930 | PRO | 66 | ca | 0.0600 | 325 |
| HA | 27.989650726 | 26.634012222 | 77.917152405 | PRO | 66 | h | 0.1000 | 326 |
| CD | 28.016592026 | 28.532529831 | 80.511337280 | PRO | 66 | c2 | 0.0600 | 327 |
| HD1 | 27.731332779 | 29.536006927 | 80.880874634 | PRO | 66 | h | 0.1000 | 328 |
| HD2 | 29.027824402 | 28.301166534 | 80.897590637 | PRO | 66 | h | 0.1000 | 329 |
| C | 25.977466583 | 27.479314804 | 77.725341797 | PRO | 66 | c' | 0.3800 | 330 |
| O | 25.217950821 | 28.417282104 | 77.982574463 | PRO | 66 | o' | -0.3800 | 331 |
| CB | 27.045602798 | 26.422634125 | 79.851196289 | PRO | 66 | c2 | -0.2000 | 332 |
| HB1 | 26.132562637 | 25.797079086 | 79.827728271 | PRO | 66 | h | 0.1000 | 333 |
| HB2 | 27.890687943 | 25.729280472 | 80.029365540 | PRO | 66 | h | 0.1000 | 334 |
| CG | 27.003501892 | 27.477243423 | 80.958015442 | PRO | 66 | c2 | -0.2000 | 335 |
| HG1 | 25.990892410 | 27.921483994 | 81.014678955 | PRO | 66 | h | 0.1000 | 336 |
| HG2 | 27.232566833 | 27.061700821 | 81.956459045 | PRO | 66 | h | 0.1000 | 337 |
| N | 25.734319687 | 26.626403809 | 76.719802856 | ARG+ | 67 | n | -0.5000 | 338 |
| CA | 24.603988647 | 26.793025970 | 75.767257690 | ARG+ | 67 | ca | 0.1200 | 339 |
| HN | 26.386735916 | 25.841371536 | 76.649803162 | ARG+ | 67 | hn | 0.2800 | 340 |
| HA | 24.496238708 | 27.874828339 | 75.561668396 | ARG+ | 67 | h | 0.1000 | 341 |
| C | 23.227464676 | 26.224872589 | 76.267372131 | ARG+ | 67 | c' | 0.3800 | 342 |
| O | 23.178310394 | 25.034952164 | 76.603759766 | ARG+ | 67 | o' | -0.3800 | 343 |
| CB | 24.990058899 | 26.165229797 | 74.398826599 | ARG+ | 67 | c2 | -0.2000 | 344 |
| HB1 | 24.135663986 | 26.318639755 | 73.709175110 | ARG+ | 67 | h | 0.1100 | 345 |
| HB2 | 25.787433624 | 26.779323578 | 73.940032959 | ARG+ | 67 | h | 0.1100 | 346 |
| CG | 25.439929962 | 24.676465988 | 74.361564636 | ARG+ | 67 | c2 | -0.2000 | 347 |
| HG1 | 26.546255112 | 24.646316528 | 74.415458679 | ARG+ | 67 | h | 0.1300 | 348 |
| HG2 | 25.092346191 | 24.131168365 | 75.261718750 | ARG+ | 67 | h | 0.1300 | 349 |
| CD | 24.934387207 | 23.941221237 | 73.112297058 | ARG+ | 67 | c2 | -0.0900 | 350 |
| HD1 | 23.838283539 | 23.774566650 | 73.188652039 | ARG+ | 67 | h | 0.1300 | 351 |
| HD2 | 25.070211411 | 24.585262299 | 72.220893860 | ARG+ | 67 | h | 0.1300 | 352 |
| NE | 25.665744781 | 22.657058716 | 72.968780518 | ARG+ | 67 | n1 | -0.5000 | 353 |
| HE | 36.251846313 | 22.313375473 | 73.731925964 | ARG+ | 67 | hn | 0.3600 | 354 |
| CZ | 25.689014435 | 21.902687073 | 71.871635437 | ARG+ | 67 | cr | 0.4500 | 355 |
| NH1 | 26.493299484 | 20.879484177 | 71.859733582 | ARG+ | 67 | n2 | -0.5000 | 356 |
| HH11 | 27.072675705 | 20.740955353 | 72.690315247 | ARG+ | 67 | hn | 0.3600 | 357 |
| HH12 | 26.520929337 | 20.319580078 | 71.006805420 | ARG+ | 67 | hn | 0.3600 | 358 |
| NH2 | 24.956668854 | 22.117029190 | 70.805320740 | ARG+ | 67 | n2 | -0.5000 | 359 |
| HH21 | 25.030595779 | 21.456792831 | 70.033142090 | ARG+ | 67 | hn | 0.3600 | 360 |
| HH22 | 24.266489029 | 22.916227341 | 70.850784302 | ARG+ | 67 | hn | 0.3600 | 361 |
| N | 22.080270767 | 26.971176147 | 76.244255066 | PRO | 68 | n | -0.4200 | 362 |
| CA | 20.743734360 | 26.358839035 | 76.485237122 | PRO | 68 | ca | 0.0600 | 363 |
| HA | 20.817556381 | 25.605155945 | 77.294357300 | PRO | 68 | h | 0.1000 | 364 |
| CD | 22.076143265 | 28.448001862 | 76.342918396 | PRO | 68 | c2 | 0.0600 | 365 |
| HD1 | 22.539228439 | 28.949869156 | 75.469612122 | PRO | 68 | h | 0.1000 | 366 |
| HD2 | 22.632146835 | 28.776126862 | 77.244499207 | PRO | 68 | h | 0.1000 | 367 |
| C | 20.182382584 | 25.586124692 | 75.240180969 | PRO | 68 | c' | 0.3800 | 368 |
| O | 20.420539856 | 24.381649017 | 75.139877319 | PRO | 68 | o' | -0.3800 | 369 |
| CB | 19.948141098 | 27.549791336 | 77.062515259 | PRO | 68 | c2 | -0.2000 | 370 |
| HB1 | 18.858430862 | 27.490163803 | 76.877128601 | PRO | 68 | h | 0.1000 | 371 |
| HB2 | 20.066789627 | 27.567596436 | 78.163002014 | PRO | 68 | h | 0.1000 | 372 |
| CG | 20.592071533 | 28.804227829 | 76.467758179 | PRO | 68 | c2 | -0.2000 | 373 |
| HG1 | 20.158363342 | 29.031393051 | 75.478172302 | PRO | 68 | h | 0.1000 | 374 |
| HG2 | 20.428398132 | 29.704229355 | 77.092338562 | PRO | 68 | h | 0.1000 | 375 |
| N | 19.458055496 | 26.229068756 | 74.300010681 | ARG+ | 69 | n | -0.5000 | 376 |
| CA | 18.893756866 | 25.542047501 | 73.096710205 | ARG+ | 69 | ca | 0.1200 | 377 |
| HN | 19.221296310 | 27.198928833 | 74.529014587 | ARG+ | 69 | hn | 0.2800 | 378 |
| HA | 19.667610168 | 24.872461319 | 72.660797119 | ARG+ | 69 | h | 0.1000 | 379 |
| C | 18.514461517 | 26.608341217 | 72.012504578 | ARG+ | 69 | c' | 0.3800 | 380 |
| O | 17.383218765 | 27.099323273 | 72.036094666 | ARG+ | 69 | o' | -0.3800 | 381 |
| CB | 17.681777954 | 24.654710770 | 73.539657593 | ARG+ | 69 | c2 | -0.2000 | 382 |
| HB1 | 18.011884689 | 23.935596466 | 74.315147400 | ARG+ | 69 | h | 0.1100 | 383 |
| HB2 | 16.954420090 | 25.310214996 | 74.061965942 | ARG+ | 69 | h | 0.1100 | 384 |
| CG | 16.946891785 | 23.862810135 | 72.427490234 | ARG+ | 69 | c2 | -0.2000 | 385 |
| HG1 | 16.649517059 | 24.551628113 | 71.612152100 | ARG+ | 69 | h | 0.1300 | 386 |
| HG2 | 17.638776779 | 23.127803802 | 71.965805054 | ARG+ | 69 | h | 0.1300 | 387 |
| CD | 15.688191414 | 23.166488647 | 72.975959778 | ARG+ | 69 | c2 | -0.0900 | 388 |
| HD1 | 15.980383873 | 22.365550995 | 73.686569214 | ARG+ | 69 | h | 0.1300 | 389 |
| HD2 | 15.090404510 | 23.898859024 | 73.554351807 | ARG+ | 69 | h | 0.1300 | 390 |
| NE | 14.889810562 | 22.612804413 | 71.848815918 | ARG+ | 69 | n1 | -0.5000 | 391 |
| HE | 15.272388458 | 22.616128922 | 70.898582458 | ARG+ | 69 | hn | 0.3600 | 392 |
| CZ | 13.644455910 | 22.143890381 | 71.942466736 | ARG+ | 69 | cr | 0.4500 | 393 |
| NH1 | 13.048615456 | 21.755460739 | 70.850708008 | ARG+ | 69 | n2 | -0.5000 | 394 |
| HH11 | 13.576630592 | 21.832328796 | 69.979103088 | ARG+ | 69 | hn | 0.3600 | 395 |
| HH12 | 12.090744019 | 21.411947250 | 70.936080933 | ARG+ | 69 | hn | 0.3600 | 396 |
| NH2 | 12.989639282 | 22.056533813 | 73.074882507 | ARG+ | 69 | n2 | -0.5000 | 397 |
| HH21 | 12.033639908 | 21.696094513 | 73.066261292 | ARG+ | 69 | hn | 0.3600 | 398 |

TABLE No. 1-continued

| Atom name | x | y | z | residue name and no. | | atom type, charge and no. | |
|---|---|---|---|---|---|---|---|
| HH22 | 13.529273987 | 22.372974396 | 73.883934021 | ARG+ | 69 hn | 0.3600 | 399 |
| N | 19.436628342 | 26.928932190 | 71.074501038 | ARG+ | 70 n | −0.5000 | 400 |
| CA | 19.223009109 | 27.811206818 | 69.878326416 | ARG+ | 70 ca | 0.1200 | 401 |
| HN | 20.357131958 | 26.451332092 | 71.165985107 | ARG+ | 70 hn | 0.2800 | 402 |
| HA | 19.087514877 | 27.065124512 | 69.071128845 | ARG+ | 70 h | 0.1000 | 403 |
| C | 20.512538910 | 28.575149536 | 69.398536682 | ARG+ | 70 c' | 0.3800 | 404 |
| O | 20.872812271 | 28.468791962 | 68.228363037 | ARG+ | 70 o' | −0.3800 | 405 |
| CB | 17.935552597 | 28.697717667 | 69.732887268 | ARG+ | 70 c2 | −0.2000 | 406 |
| HB1 | 17.889257431 | 29.085472107 | 68.694030762 | ARG+ | 70 h | 0.1100 | 407 |
| HB2 | 17.053388596 | 28.033058167 | 69.807891846 | ARG+ | 70 h | 0.1100 | 408 |
| CG | 17.775762558 | 29.883768082 | 70.717842102 | ARG+ | 70 c2 | −0.2000 | 409 |
| HG1 | 18.004568100 | 29.546030045 | 71.747383118 | ARG+ | 70 h | 0.1300 | 410 |
| HG2 | 18.540782928 | 30.651863098 | 70.495643616 | ARG+ | 70 h | 0.1300 | 411 |
| CD | 16.368116379 | 30.502414703 | 70.693214417 | ARG+ | 70 c2 | −0.0900 | 412 |
| HD1 | 16.095691681 | 30.812221527 | 69.664886475 | ARG+ | 70 h | 0.1300 | 413 |
| HD2 | 15.630161285 | 29.711160660 | 70.937812805 | ARG+ | 70 h | 0.1300 | 414 |
| NE | 16.255954742 | 31.590759277 | 71.711013794 | ARG+ | 70 n1 | −0.5000 | 415 |
| HE | 16.253637314 | 31.350564957 | 72.706428528 | ARG+ | 70 hn | 0.3600 | 416 |
| CZ | 16.144437790 | 32.900745392 | 71.464541462 | ARG+ | 70 cr | 0.4500 | 417 |
| NH1 | 16.055492401 | 33.712890625 | 72.481109619 | ARG+ | 70 n2 | −0.5000 | 418 |
| HH11 | 16.071464539 | 33.294216156 | 73.433330078 | ARG+ | 70 hn | 0.3600 | 419 |
| HH12 | 15.975571632 | 34.708621979 | 72.277374268 | ARG+ | 70 hn | 0.3600 | 420 |
| NH2 | 16.120351791 | 33.420074463 | 70.259872437 | ARG+ | 70 n2 | −0.5000 | 421 |
| HH21 | 16.025018692 | 34.432674408 | 70.167800903 | ARG+ | 70 hn | 0.3600 | 422 |
| HH22 | 16.187112808 | 32.736862183 | 69.505996704 | ARG+ | 70 hn | 0.3600 | 423 |
| N | 21.115812302 | 29.562902451 | 70.071769714 | TYRC | 71 n | −0.5000 | 424 |
| HN | 21.515977859 | 30.157514572 | 69.338050842 | TYRC | 71 hn | 0.2800 | 425 |
| CA | 22.034273148 | 29.314456940 | 71.218978882 | TYRC | 71 ca | 0.1200 | 426 |
| HA | 22.671009064 | 28.444923401 | 70.976676941 | TYRC | 71 h | 0.1000 | 427 |
| C | 21.352920532 | 28.953493118 | 72.563385010 | TYRC | 71 c' | 0.4100 | 428 |
| OXT | 20.392858505 | 29.553161621 | 73.048652649 | TYRC | 71 o' | −0.3800 | 429 |
| O | 21.928325653 | 27.853042603 | 73.145797729 | TYRC | 71 oh | −03800 | 430 |
| HO | 21.429273605 | 27.558662415 | 73.909782410 | TYRC | 71 ho | 0.3500 | 431 |
| CB | 22.969152451 | 30.555358887 | 71.361984253 | TYRC | 71 c2 | −0.2000 | 432 |
| HB1 | 22.368267059 | 31.487627029 | 71.355415344 | TYRC | 71 h | 0.1000 | 433 |
| HB2 | 23.401992798 | 30.559690475 | 72.381835938 | TYRC | 71 h | 0.1000 | 434 |
| CG | 24.144546509 | 30.666173935 | 70.352111816 | TYRC | 71 cp | 0.0000 | 435 |
| CD1 | 23.927837372 | 31.126276016 | 69.044418335 | TYRC | 71 cp | −0.1000 | 436 |
| HD1 | 22.944635391 | 31.424867630 | 68.717597961 | TYRC | 71 h | 0.1000 | 437 |
| CE1 | 24.987041473 | 31.212265015 | 68.143028259 | TYRC | 71 cp | −0.1000 | 438 |
| HE1 | 24.819047928 | 31.555503845 | 67.131973267 | TYRC | 71 h | 0.1000 | 439 |
| CZ | 26.273118973 | 30.861675262 | 68.542274475 | TYRC | 71 cp | 0.0300 | 440 |
| OH | 27.314481735 | 30.957365036 | 67.652267456 | TYRC | 71 oh | −0.3800 | 441 |
| HH | 26.980180740 | 31.236070633 | 66.796859741 | TYRC | 71 ho | 0.3500 | 442 |
| CE2 | 26.504697800 | 30.422637939 | 69.841377258 | TYRC | 71 cp | −0.1000 | 443 |
| HE2 | 27.503232956 | 30.148866653 | 70.140815735 | TYRC | 71 h | 0.1000 | 444 |
| CD2 | 25.447391510 | 30.325349808 | 70.743820190 | TYRC | 71 cp | −0.1000 | 445 |
| HD2 | 25.652494431 | 29.968608856 | 71.745338440 | TYRC | 71 h | 0.1000 | 430 |

TABLE No. 2

| Atom name | x | y | z | residue name and no. | | atom type, charge and no. | |
|---|---|---|---|---|---|---|---|
| N | 24.753738403 | 26.435615540 | 68.244300842 | CYSn | 40 n3 | −0.5000 | 1 |
| CA | 24.503000259 | 26.356292725 | 69.707687378 | CYSn | 40 ca | 0.1200 | 2 |
| HN1 | 23.861560822 | 26.429992676 | 67.734397888 | CYSn | 40 hn | 0.1400 | 3 |
| HN2 | 25.250690460 | 25.603431424 | 67.909477234 | CYSn | 40 hn | 0.1400 | 4 |
| HA | 23.890571594 | 27.247760773 | 69.940788269 | CYSn | 40 h | 0.1000 | 5 |
| C | 25.747190475 | 26.505004883 | 70.632949829 | CYSn | 40 c' | 0.3800 | 6 |
| O | 25.611124039 | 27.204542160 | 71.634971619 | CYSn | 40 o' | −0.3800 | 7 |
| CB | 23.602088928 | 25.125436783 | 69.979545593 | CYSn | 40 c2 | −0.3000 | 8 |
| HB1 | 22.555475235 | 25.378625870 | 69.716011047 | CYSn | 40 h | 0.1000 | 9 |
| HB2 | 23.865217209 | 24.277284622 | 69.317871094 | CYSn | 40 h | 0.1000 | 10 |
| SG | 23.613842010 | 24.466741562 | 71.679084778 | CYSn | 40 s1 | 0.1000 | 11 |
| N | 26.910152435 | 25.881416321 | 70.350471497 | SER | 41 n | −0.5000 | 12 |
| CA | 28.052598953 | 25.721015930 | 71.310394287 | SER | 41 ca | 0.1200 | 13 |
| HN | 26.921674728 | 25.473436356 | 69.412322998 | SER | 41 hn | 0.2800 | 14 |
| HA | 27.761577606 | 24.886217117 | 71.978584290 | SER | 41 h | 0.1000 | 15 |
| C | 28.477056503 | 26.929338455 | 72.226699829 | SER | 41 c' | 0.3800 | 16 |
| O | 28.412267685 | 28.097608566 | 71.829902649 | SER | 41 o' | −0.3800 | 17 |

TABLE No. 2-continued

| Atom name | x | y | z | residue name and no. | | atom type, charge and no. | | |
|---|---|---|---|---|---|---|---|---|
| CB | 29.257335663 | 25.212779999 | 70.480110168 | SER | 41 | c2 | −0.1700 | 18 |
| HB1 | 28.957101822 | 24.401222229 | 69.786743164 | SER | 41 | h | 0.1000 | 19 |
| HB2 | 29.657680511 | 26.030597687 | 69.845893860 | SER | 41 | h | 0.1000 | 20 |
| OG | 30.284814835 | 24.713315964 | 71.339111328 | SER | 41 | oh | −0.3800 | 21 |
| HG | 31.027490616 | 24.448732376 | 70.785003662 | SER | 41 | ho | 0.3500 | 22 |
| N | 28.904022217 | 26.617259979 | 73.466476440 | GLY | 42 | n | −0.5000 | 23 |
| CA | 29.226711273 | 27.639400482 | 74.497131348 | GLY | 42 | cg | 0.0200 | 24 |
| HN | 29.140472412 | 25.626163483 | 73.587532043 | GLY | 42 | hn | 0.2800 | 25 |
| HA1 | 28.567264557 | 28.519987106 | 74.394309998 | GLY | 42 | h | 0.1000 | 26 |
| HA2 | 28.949186325 | 27.229663849 | 75.483924866 | GLY | 42 | h | 0.1000 | 27 |
| C | 30.728670120 | 28.040773392 | 74.587509155 | GLY | 42 | c' | 0.3800 | 28 |
| O | 31.522300720 | 27.171119690 | 74.941143494 | GLY | 42 | o' | −0.3800 | 29 |
| N | 31.175983429 | 29.296203613 | 74.282577515 | PRO | 43 | n | −0.4200 | 30 |
| CA | 32.627410889 | 29.612504959 | 74.140579224 | PRO | 43 | ca | 0.0600 | 31 |
| HA | 33.153442383 | 28.731788635 | 73.723632813 | PRO | 43 | h | 0.1000 | 32 |
| CD | 30.395356750 | 30.374078751 | 73.784042358 | PRO | 43 | c2 | 0.0600 | 33 |
| HD1 | 29.605636597 | 30.735929489 | 74.571166992 | PRO | 43 | h | 0.1000 | 34 |
| HD2 | 29.683467865 | 30.026647568 | 72.928161621 | PRO | 43 | h | 0.1000 | 35 |
| C | 33.389945984 | 30.112844467 | 75.429031372 | PRO | 43 | c' | 0.3800 | 36 |
| O | 32.754360199 | 30.681560516 | 76.327354431 | PRO | 43 | o' | −0.3800 | 37 |
| CB | 32.565906525 | 30.710325241 | 73.057388306 | PRO | 43 | c2 | −0.2000 | 38 |
| HB1 | 33.449081421 | 31.378034592 | 73.055488586 | PRO | 43 | h | 0.1000 | 39 |
| HB2 | 32.524932861 | 30.247560501 | 72.051818848 | PRO | 43 | h | 0.1000 | 40 |
| CG | 31.263490677 | 31.466632843 | 73.332626343 | PRO | 43 | c2 | −0.2000 | 41 |
| HG1 | 31.413110733 | 32.204200745 | 74.146759033 | PRO | 43 | h | 0.1000 | 42 |
| HG2 | 30.894020081 | 32.022109985 | 72.450286865 | PRO | 43 | h | 0.1000 | 43 |
| N | 34.754848480 | 30.015562057 | 75.523460388 | PRO | 44 | n | −0.4200 | 44 |
| CA | 35.553565979 | 30.763086319 | 76.536285400 | PRO | 44 | ca | 0.0600 | 45 |
| HA | 35.083564758 | 30.695350647 | 77.536567688 | PRO | 44 | h | 0.1000 | 46 |
| CD | 35.574893951 | 29.135835648 | 74.665214539 | PRO | 44 | c2 | 0.0600 | 47 |
| HD1 | 35.471595764 | 29.373666763 | 73.588935852 | PRO | 44 | h | 0.1000 | 48 |
| HD2 | 35.281650543 | 28.076414108 | 74.807395935 | PRO | 44 | h | 0.1000 | 49 |
| C | 35.767509460 | 32.265411377 | 76.141113281 | PRO | 44 | c' | 0.3800 | 50 |
| O | 36.544441223 | 32.599441528 | 75.238464355 | PRO | 44 | o' | −0.3800 | 51 |
| CB | 36.849227905 | 29.927103043 | 76.567779541 | PRO | 44 | c2 | −0.2000 | 52 |
| HB1 | 37.732776642 | 30.502979279 | 76.899009705 | PRO | 44 | h | 0.1000 | 53 |
| HB2 | 36.733722687 | 29.095364598 | 77.289833069 | PRO | 44 | h | 0.1000 | 54 |
| CG | 37.005489349 | 29.369808197 | 75.152618408 | PRO | 44 | c2 | −0.2000 | 55 |
| HG1 | 37.502185822 | 30.119005203 | 74.504158020 | PRO | 44 | h | 0.1000 | 56 |
| HG2 | 37.625408173 | 28.451385498 | 75.115615645 | PRO | 44 | h | 0.1000 | 57 |
| N | 35.047088623 | 33.173435211 | 76.826978455 | ALA | 45 | n | −0.5000 | 58 |
| CA | 35.011333466 | 34.609920502 | 76.449218750 | ALA | 45 | ca | 0.1200 | 59 |
| HN | 34.471405029 | 32.798248291 | 77.590728760 | ALA | 45 | hn | 0.2800 | 60 |
| HA | 35.065380096 | 34.699813843 | 75.343650818 | ALA | 45 | h | 0.1000 | 61 |
| C | 36.187728882 | 35.414947510 | 77.090148926 | ALA | 45 | c' | 0.3800 | 62 |
| O | 36.133388519 | 35.819305420 | 78.255142212 | ALA | 45 | o' | −0.3800 | 63 |
| CB | 33.615478516 | 35.135440826 | 76.831176758 | ALA | 45 | c3 | −0.3000 | 64 |
| HB1 | 33.490375519 | 36.187480927 | 76.517280579 | ALA | 45 | h | 0.1000 | 65 |
| HB2 | 32.811222076 | 34.556259155 | 76.338432312 | ALA | 45 | h | 0.1000 | 66 |
| HB3 | 33.433517456 | 35.098365784 | 77.922439575 | ALA | 45 | h | 0.1000 | 67 |
| N | 37.264499664 | 35.613868713 | 76.306388855 | ALA | 46 | n | −0.5000 | 68 |
| HN | 37.248832703 | 35.072978973 | 75.433502197 | ALA | 46 | hn | 0.2800 | 69 |
| CA | 38.503662109 | 36.298694611 | 76.764076233 | ALA | 46 | ca | 0.1200 | 70 |
| HA | 38.303600311 | 36.883266449 | 77.688095093 | ALA | 46 | h | 0.1000 | 71 |
| C | 39.082061768 | 37.273509979 | 75.687866211 | ALA | 46 | c' | 0.3800 | 72 |
| O | 38.951850891 | 37.052509308 | 74.481193542 | ALA | 46 | o' | −0.3800 | 73 |
| CB | 39.509185791 | 35.179004669 | 77.103065491 | ALA | 46 | c3 | −0.3000 | 74 |
| HB1 | 40.441535950 | 35.582756042 | 77.535072327 | ALA | 46 | h | 01000 | 75 |
| HB2 | 39.106670380 | 34.460605621 | 77.839447021 | ALA | 46 | h | 0.1000 | 76 |
| HB3 | 39.780502319 | 34.597728729 | 76.205062866 | ALA | 46 | h | 0.1000 | 77 |
| N | 39.768814087 | 38.344066620 | 76.133750916 | ALA | 47 | n | −0.5000 | 78 |
| CA | 40.322643280 | 39.391151428 | 75.225708008 | ALA | 47 | ca | 0.1200 | 79 |
| HN | 39.783836365 | 38.455593109 | 77.149337769 | ALA | 47 | hn | 0.2800 | 80 |
| HA | 39.932807922 | 39.265201569 | 74.196365356 | ALA | 47 | h | 0.1000 | 81 |
| C | 41.900882721 | 39.401374817 | 75.126907349 | ALA | 47 | c' | 0.3800 | 82 |
| O | 42.538444519 | 40.171451569 | 75.854652405 | ALA | 47 | o' | −0.3800 | 83 |
| CB | 39.728843689 | 40.731719971 | 75.714279175 | ALA | 47 | c3 | −0.3000 | 84 |
| HB1 | 40.043342590 | 41.567916870 | 75.059875488 | ALA | 47 | h | 0.1000 | 85 |
| HB2 | 38.621978760 | 40.726497650 | 75.711242676 | ALA | 47 | h | 0.1000 | 86 |
| HB3 | 40.062076569 | 40.987442017 | 76.739311218 | ALA | 47 | h | 0.1000 | 87 |
| N | 42.578651428 | 38.603939056 | 74.242019653 | PRO | 48 | n | −0.4200 | 88 |
| CA | 44.052474976 | 38.702857971 | 74.013595581 | PRO | 48 | ca | 0.0600 | 89 |
| HA | 44.576034546 | 38.850185394 | 74.977058411 | PRO | 48 | h | 0.1000 | 90 |
| CD | 41.956359863 | 37.474979401 | 73.520225525 | PRO | 48 | c2 | 0.0600 | 91 |
| HD1 | 41.114963531 | 37.788272858 | 72.872795105 | PRO | 48 | h | 0.1000 | 92 |

TABLE No. 2-continued

| Atom name | x | y | z | residue name and no. | | atom type, charge and no. | |
|---|---|---|---|---|---|---|---|
| HD2 | 41.576156616 | 36.723818915 | 74.239135742 | PRO | 48 h | 0.1000 | 93 |
| C | 44.492458344 | 39.820354462 | 73.002609253 | PRO | 48 c' | 0.3800 | 94 |
| O | 43.782276154 | 40.131282806 | 72.040626526 | PRO | 48 o' | −0.3800 | 95 |
| CB | 44.356296539 | 37.289741516 | 73.479736328 | PRO | 48 c2 | −0.2000 | 96 |
| HB1 | 45.273612976 | 37.234390259 | 72.865592957 | PRO | 48 h | 0.1000 | 97 |
| HB2 | 44.513816833 | 36.591526031 | 74.332021484 | PRO | 48 h | 0.1000 | 98 |
| CG | 43.102409363 | 36.884414673 | 72.700988770 | PRO | 48 c2 | −0.2000 | 99 |
| HG1 | 43.119277954 | 37.331111908 | 71.685241699 | PRO | 48 h | 0.1000 | 100 |
| HG2 | 43.010280609 | 35.788948059 | 72.572326660 | PRO | 48 h | 0.1000 | 101 |
| N | 45.709655762 | 40.366821289 | 73.185493469 | GLY | 49 n | −0.5000 | 102 |
| CA | 46.317604065 | 41.332912445 | 73.214889526 | GLY | 49 cg | 0.0200 | 103 |
| HN | 46.169986725 | 40.089691162 | 74.058357239 | GLY | 49 hn | 0.2800 | 104 |
| HA1 | 45.654991150 | 41.537052155 | 71.351181030 | GLY | 49 h | 0.1000 | 105 |
| HA2 | 46.406318665 | 42.313266754 | 72.719123840 | GLY | 49 h | 0.1000 | 106 |
| C | 47.710880280 | 40.963481903 | 71.654037476 | GLY | 49 c' | 0.3800 | 107 |
| O | 48.630664825 | 41.772521973 | 71.754951477 | GLY | 49 o' | −0.3800 | 108 |
| N | 47.830738068 | 39.763301849 | 71.063682556 | HIS | 50 n | −0.5000 | 109 |
| HN | 46.918842316 | 39.310573578 | 70.943237305 | HIS | 50 hn | 0.2800 | 110 |
| CA | 49.045799255 | 39.210880280 | 70.375061035 | HIS | 50 ca | 0.1200 | 111 |
| HA | 49.315334320 | 38.320884705 | 70.972137451 | HIS | 50 h | 0.1000 | 112 |
| C | 50.433021545 | 39.981941223 | 70.267852783 | HIS | 50 c' | 0.3800 | 113 |
| O | 50.773132324 | 40.456230164 | 69.178672791 | HIS | 50 o' | −0.3800 | 114 |
| CB | 48.558776855 | 38.590164185 | 69.024101257 | HIS | 50 c2 | −0.2000 | 115 |
| HB1 | 49.390335083 | 36.009521484 | 68.577232361 | HIS | 50 h | 0.1000 | 116 |
| HB2 | 47.792594910 | 37.817192078 | 69.227310181 | HIS | 50 h | 0.1000 | 117 |
| CG | 47.997627258 | 39.545143127 | 67.956726074 | HIS | 50 c5 | 0.1000 | 118 |
| ND1 | 46.669281006 | 39.956676483 | 67.918121338 | HIS | 50 np | −0.4200 | 119 |
| CE1 | 46.730144501 | 40.789539337 | 66.829002380 | HIS | 50 c5 | 0.2700 | 120 |
| NE2 | 47.911670685 | 40.950614929 | 66.152328491 | HIS | 50 np | −0.5000 | 121 |
| CD2 | 48.729324341 | 40.126430511 | 66.904235840 | HIS | 50 c5 | 0.0100 | 122 |
| HE1 | 45.843067169 | 41.327060699 | 66.517631531 | HIS | 50 h | 0.1300 | 123 |
| HE2 | 48.138290405 | 41.548683167 | 65.349815369 | HIS | 50 hn | 0.2800 | 124 |
| HD2 | 49.789726257 | 39.981491089 | 66.738136292 | HIS | 50 h | 0.1300 | 125 |
| N | 51.307849884 | 40.071182251 | 71.317932129 | PRO | 51 n | −0.4200 | 126 |
| CA | 52.692558289 | 40.596851349 | 71.184913635 | PRO | 51 ca | 0.0600 | 127 |
| HA | 52.742668152 | 41.390510559 | 70.412712097 | PRO | 51 h | 0.1000 | 128 |
| CD | 50.980678558 | 39.703777313 | 72.706970215 | PRO | 51 c2 | 0.0600 | 129 |
| HD1 | 50.998199463 | 38.605384827 | 72.818397522 | PRO | 51 h | 0.1000 | 130 |
| HD2 | 49.987606049 | 40.071315765 | 73.019950867 | PRO | 51 h | 0.1000 | 131 |
| C | 53.739063263 | 39.471630096 | 70.880722046 | PRO | 51 c' | 0.3800 | 132 |
| O | 53.708900452 | 38.394466400 | 71.488830566 | PRO | 51 o' | −0.3800 | 133 |
| CB | 52.868911743 | 41.240936279 | 72.572486877 | PRO | 51 c2 | −0.2000 | 134 |
| HB1 | 53.929355621 | 41.364253998 | 72.864852905 | PRO | 51 h | 0.1000 | 135 |
| HB2 | 52.429229736 | 42.258647919 | 72.565872192 | PRO | 51 h | 0.1000 | 136 |
| CG | 52.087848663 | 40.349472046 | 73.547019958 | PRO | 51 c2 | −0.2000 | 137 |
| HG1 | 52.750400543 | 39.566276550 | 73.963310242 | PRO | 51 h | 0.1000 | 138 |
| HG2 | 51.686916351 | 40.923263550 | 74.403717041 | PRO | 51 h | 0.1000 | 139 |
| N | 54.676445007 | 39.726749420 | 69.946899414 | LEU | 52 n | −0.5000 | 140 |
| CA | 55.768096924 | 38.764469147 | 69.570259094 | LEU | 52 ca | 0.1200 | 141 |
| HN | 54.573589325 | 40.637012482 | 69.488586426 | LEU | 52 hn | 0.2800 | 142 |
| HA | 56.414031982 | 39.325927734 | 68.869346619 | LEU | 52 h | 0.1000 | 143 |
| C | 55.281269073 | 37.540004730 | 68.718757629 | LEU | 52 c' | 0.3800 | 144 |
| O | 55.654800415 | 37.411125183 | 67.550910950 | LEU | 52 o' | −0.3800 | 145 |
| CB | 56.713882446 | 38.354763031 | 70.751991272 | LEU | 52 c2 | −0.2000 | 146 |
| HB1 | 56.125553131 | 37.737205505 | 71.456863403 | LEU | 52 h | 0.1000 | 147 |
| HB2 | 57.488136292 | 37.658962250 | 70.374801636 | LEU | 52 h | 0.1000 | 148 |
| CG | 57.411731720 | 39.487998962 | 71.552589417 | LEU | 52 c1 | −0.1000 | 149 |
| HG | 56.652648926 | 40.244640350 | 71.834617615 | LEU | 52 h | 0.1000 | 150 |
| CD1 | 58.010108948 | 38.936943054 | 72.859535217 | LEU | 52 c3 | −0.3000 | 151 |
| HD11 | 58.475826263 | 39.735752106 | 73.467353821 | LEU | 52 h | 0.1000 | 152 |
| HD12 | 57.236072540 | 38.469894409 | 73.497505188 | LEU | 52 h | 0.1000 | 153 |
| HD13 | 58.787303925 | 38.171112061 | 72.675750732 | LEU | 52 h | 0.1000 | 154 |
| CD2 | 58.517623901 | 40.187110901 | 70.742630005 | LEU | 52 c3 | −0.3000 | 155 |
| HD21 | 58.993679047 | 41.001243591 | 71.321037292 | LEU | 52 h | 0.1000 | 156 |
| HD22 | 59.321178436 | 39.487018585 | 70.445312500 | LEU | 52 h | 0.1000 | 157 |
| HD23 | 58.125030518 | 40.647811890 | 69.818283081 | LEU | 52 h | 0.1000 | 158 |
| N | 54.475013733 | 36.643035889 | 69.315246582 | ALA | 53 n | −0.5000 | 159 |
| CA | 53.896503448 | 35.451416016 | 68.639259338 | ALA | 53 ca | 0.1200 | 160 |
| HN | 54.100524902 | 37.007503510 | 70.205230713 | ALA | 53 hn | 0.2800 | 161 |
| HA | 53.553531647 | 35.773445129 | 67.634338379 | ALA | 53 h | 0.1000 | 162 |
| C | 52.602260590 | 34.908508301 | 69.353744507 | ALA | 53 c' | 0.3800 | 163 |
| O | 51.589202881 | 34.828308105 | 68.650034414 | ALA | 53 o' | −0.3800 | 164 |
| CB | 54.970031738 | 34.364234924 | 68.394615173 | ALA | 53 c3 | −0.3000 | 165 |
| HB1 | 54.534633636 | 33.449993134 | 67.949813843 | ALA | 53 h | 0.1000 | 166 |
| HB2 | 55.742454529 | 34.720954895 | 67.688003540 | ALA | 53 h | 0.1000 | 167 |

TABLE No. 2-continued

| Atom name | x | y | z | residue name and no. | | atom type, charge and no. | | |
|---|---|---|---|---|---|---|---|---|
| HB3 | 55.500236511 | 34.068145752 | 69.316299438 | ALA | 53 | h | 0.1000 | 168 |
| N | 52.528438568 | 34.519321442 | 70.670852661 | PRO | 54 | n | −0.4200 | 169 |
| CA | 51.288402557 | 33.944232941 | 71.268875122 | PRO | 54 | ca | 0.0600 | 170 |
| HA | 50.860397339 | 33.194515228 | 70.573081970 | PRO | 54 | h | 0.1000 | 171 |
| CD | 53.678298950 | 34.513732910 | 71.601814270 | PRO | 54 | c2 | 0.0600 | 172 |
| HD1 | 54.146690369 | 35.509193420 | 71.717323303 | PRO | 54 | h | 0.1000 | 173 |
| HD2 | 54.456859589 | 33.804187775 | 71.264945984 | PRO | 54 | h | 0.1000 | 174 |
| C | 50.163700104 | 34.973747253 | 71.631500244 | PRO | 54 | c' | 0.3800 | 175 |
| O | 50.381851196 | 36.186935425 | 71.709472656 | PRO | 54 | o' | −0.3800 | 176 |
| CB | 51.868888855 | 33.209735870 | 72.497810364 | PRO | 54 | c2 | −0.2000 | 177 |
| HB1 | 51.140216827 | 33.071922302 | 73.319641113 | PRO | 54 | h | 0.1000 | 178 |
| HB2 | 52.201725006 | 32.193626404 | 72.207275391 | PRO | 54 | h | 0.1000 | 179 |
| CG | 53.074722290 | 34.047100067 | 72.925216675 | PRO | 54 | c2 | −0.2000 | 180 |
| HG1 | 52.742275238 | 34.920612335 | 73.520271301 | PRO | 54 | h | 0.1000 | 181 |
| HG2 | 53.794158936 | 33.482940674 | 73.547462463 | PRO | 54 | h | 0.1000 | 182 |
| N | 48.950717926 | 34.451553345 | 71.882225037 | GLY | 55 | n | −0.5000 | 183 |
| CA | 47.799011230 | 35.264900208 | 72.354187012 | GLY | 55 | cg | 0.0200 | 184 |
| HN | 48.913242340 | 33.427757263 | 71.833122253 | GLY | 55 | hn | 0.2800 | 185 |
| HA1 | 47.829734802 | 36.291049957 | 71.943481445 | GLY | 55 | h | 0.1000 | 186 |
| HA2 | 46.873668671 | 34.838825226 | 71.925086975 | GLY | 55 | h | 0.1000 | 187 |
| C | 47.624210358 | 35.262092590 | 73.898422241 | GLY | 55 | c' | 0.3800 | 188 |
| O | 47.184692383 | 34.228916168 | 74.411125183 | GLY | 55 | o' | −0.3800 | 189 |
| N | 47.910079956 | 36.345748901 | 74.679351807 | PRO | 56 | n | −0.4200 | 190 |
| CA | 47.789894104 | 36.319248199 | 76.162750244 | PRO | 56 | ca | 0.0600 | 191 |
| HA | 48.177116394 | 35.361667633 | 76.567420959 | PRO | 56 | h | 0.1000 | 192 |
| CD | 48.602729797 | 37.547939301 | 74.184982300 | PRO | 56 | c2 | 0.0600 | 193 |
| HD1 | 48.046642303 | 38.065422058 | 73.380996704 | PRO | 56 | h | 0.1000 | 194 |
| HD2 | 49.595470428 | 37.261718750 | 73.794586182 | PRO | 56 | h | 0.1000 | 195 |
| C | 46.326736450 | 36.529109955 | 76.663719177 | PRO | 56 | c' | 0.3800 | 196 |
| O | 45.857757568 | 37.657508850 | 76.842826843 | PRO | 56 | o' | −0.3800 | 197 |
| CB | 48.777050018 | 37.430667877 | 76.578651428 | PRO | 56 | c2 | −0.2000 | 198 |
| HB1 | 48.524734497 | 37.898471832 | 77.549873352 | PRO | 56 | h | 0.1000 | 199 |
| HB2 | 49.795513153 | 37.009433746 | 76.691307068 | PRO | 56 | h | 0.1000 | 200 |
| CG | 48.752750397 | 38.431644440 | 75.422836304 | PRO | 56 | c2 | −0.2000 | 201 |
| HG1 | 47.879917145 | 39.105598450 | 75.522354126 | PRO | 56 | h | 0.1000 | 202 |
| HG2 | 49.655212402 | 39.069591522 | 75.391311646 | PRO | 56 | h | 0.1000 | 203 |
| N | 45.616943359 | 35.415058136 | 76.897827148 | HIS | 57 | n | −0.5000 | 204 |
| HN | 46.014194489 | 34.579135895 | 76.450401306 | HIS | 57 | hn | 0.2800 | 205 |
| CA | 44.212440491 | 35.434158325 | 77.393867493 | HIS | 57 | ca | 0.1200 | 206 |
| HA | 43.635601044 | 36.135776520 | 76.762809753 | HIS | 57 | h | 0.1000 | 207 |
| C | 44.146274567 | 35.882919312 | 78.904235840 | HIS | 57 | c' | 0.3800 | 208 |
| O | 44.718753815 | 35.174930573 | 79.742973328 | HIS | 57 | o' | −0.3800 | 209 |
| CB | 43.577262878 | 34.025093079 | 77.198188782 | HIS | 57 | c2 | −0.2000 | 210 |
| HB1 | 44.242053986 | 33.250709534 | 77.626487732 | HIS | 57 | h | 0.1000 | 211 |
| HB2 | 42.665222168 | 33.964206696 | 77.822631836 | HIS | 57 | h | 0.1000 | 212 |
| CG | 43.190551718 | 33.606594086 | 75.770996094 | HIS | 57 | c5 | 0.1000 | 213 |
| ND1 | 44.009815216 | 33.724720001 | 74.654800415 | HIS | 57 | np | −0.4200 | 214 |
| CE1 | 43.220783234 | 33.103317261 | 73.724327087 | HIS | 57 | c5 | 0.2700 | 215 |
| NE2 | 42.000507355 | 32.603866577 | 74.087806702 | HIS | 57 | np | −0.5000 | 216 |
| CD2 | 42.008693695 | 32.921348572 | 75.433784485 | HIS | 57 | c5 | 0.0100 | 217 |
| HE1 | 43.579235077 | 32.995296478 | 72.708923340 | HIS | 57 | h | 0.1300 | 218 |
| HE2 | 41.324546814 | 32.061363220 | 73.538429260 | HIS | 57 | hn | 0.2800 | 219 |
| HD2 | 41.238662720 | 32.638732910 | 76.138023376 | HIS | 57 | h | 0.1300 | 220 |
| N | 43.493415833 | 37.014366150 | 79.314620972 | PRO | 58 | n | −0.4200 | 221 |
| CA | 43.576023102 | 37.521991730 | 80.713310242 | PRO | 58 | ca | 0.0600 | 222 |
| HA | 44.640773773 | 37.575752258 | 81.019523621 | PRO | 58 | h | 0.1000 | 223 |
| CD | 42.828823090 | 37.960189819 | 78.395561218 | PRO | 58 | c2 | 0.0600 | 224 |
| HD1 | 42.088195801 | 37.471439362 | 77.735382080 | PRO | 58 | h | 0.1000 | 225 |
| HD2 | 43.573791504 | 38.467478070 | 77.749885559 | PRO | 58 | h | 0.1000 | 226 |
| C | 42.782455444 | 36.660888672 | 81.747703552 | PRO | 58 | c' | 0.3800 | 227 |
| O | 41.546211243 | 36.662284851 | 81.766304016 | PRO | 58 | o' | −0.3800 | 228 |
| CB | 43.067096710 | 38.972381592 | 80.563407898 | PRO | 58 | c2 | −0.2000 | 229 |
| HB1 | 42.553604126 | 39.355644226 | 81.465919495 | PRO | 58 | h | 0.1000 | 230 |
| HB2 | 43.922630310 | 39.652961731 | 80.382720947 | PRO | 58 | h | 0.1000 | 231 |
| CG | 42.156223297 | 38.958541870 | 79.333923340 | PRO | 58 | c2 | −0.2000 | 232 |
| HG1 | 41.146640778 | 38.599040985 | 79.611282349 | PRO | 58 | h | 0.1000 | 233 |
| HG2 | 42.036239624 | 39.956802368 | 78.871780396 | PRO | 58 | h | 0.1000 | 234 |
| N | 43.511478424 | 35.934528351 | 82.617271423 | ALA | 59 | n | −0.5000 | 235 |
| HN | 44.509765625 | 35.905010223 | 82.386589050 | ALA | 59 | hn | 0.2800 | 236 |
| CA | 42.913761139 | 34.926112030 | 83.544029236 | ALA | 59 | ca | 0.1200 | 237 |
| HA | 42.154701233 | 34.341350555 | 82.987930298 | ALA | 59 | h | 0.1000 | 238 |
| C | 42.181308746 | 35.481468201 | 84.821502686 | ALA | 59 | c' | 0.3800 | 239 |
| O | 42.459964752 | 35.112228394 | 85.965652466 | ALA | 59 | o' | −0.3800 | 240 |
| CB | 44.063701630 | 33.948829651 | 83.858291626 | ALA | 59 | c3 | −0.3000 | 241 |
| HB1 | 43.708641052 | 33.104522705 | 84.478195190 | ALA | 59 | h | 0.1000 | 242 |

TABLE No. 2-continued

| Atom name | x | y | z | residue name and no. | | atom type, charge and no. | |
|---|---|---|---|---|---|---|---|
| HB2 | 44.502014160 | 33.503505707 | 82.944122314 | ALA | 59 | h | 0.1000 | 243 |
| HB3 | 44.882900238 | 34.433902740 | 84.422813416 | ALA | 59 | h | 0.1000 | 244 |
| N | 41.178901672 | 36.333106995 | 84.577079773 | ALA | 60 | n | -0.5000 | 245 |
| HN | 41.112052917 | 36.562049866 | 83.573013306 | ALA | 60 | hn | 0.2800 | 246 |
| CA | 40.189502716 | 36.803413391 | 85.578857422 | ALA | 60 | ca | 0.1200 | 247 |
| HA | 40.008514404 | 35.981742859 | 86.302818298 | ALA | 60 | h | 0.1000 | 248 |
| C | 38.811019897 | 37.037807465 | 84.860046387 | ALA | 60 | c' | 0.3800 | 249 |
| O | 37.881835938 | 36.301105499 | 85.205276489 | ALA | 60 | o' | -0.3800 | 250 |
| CB | 40.746566772 | 37.985549927 | 86.401313782 | ALA | 60 | c3 | -0.3000 | 251 |
| HB1 | 39.997776031 | 38.372333527 | 87.116531372 | ALA | 60 | h | 0.1000 | 252 |
| HB2 | 41.624504089 | 37.670467377 | 86.996170044 | ALA | 60 | h | 0.1000 | 253 |
| HB3 | 41.079444885 | 38.830841064 | 85.774902344 | ALA | 60 | h | 0.1000 | 254 |
| N | 38.609931946 | 37.922218323 | 83.826889038 | PRO | 61 | n | -0.4200 | 255 |
| CA | 37.398490906 | 37.873073578 | 82.950836182 | PRO | 61 | ca | 0.0600 | 256 |
| HA | 36.485267639 | 37.839759827 | 83.576164246 | PRO | 61 | h | 0.1000 | 257 |
| CD | 39.552070618 | 39.001556396 | 83.460945129 | PRO | 61 | c2 | 0.0600 | 258 |
| HD1 | 40.590957642 | 38.653537750 | 83.311111450 | PRO | 61 | h | 0.1000 | 259 |
| HD2 | 39.564563751 | 39.780746460 | 84.247795105 | PRO | 61 | h | 0.1000 | 260 |
| C | 37.256782532 | 36.700027466 | 81.909835815 | PRO | 61 | c' | 0.3800 | 261 |
| O | 36.243316650 | 36.657413483 | 81.209106445 | PRO | 61 | o' | -0.3800 | 262 |
| CB | 37.477272034 | 39.256717682 | 82.271400452 | PRO | 61 | c2 | -0.2000 | 263 |
| HB1 | 36.964195251 | 39.298637390 | 81.290786743 | PRO | 61 | h | 0.1000 | 264 |
| HB2 | 36.981357574 | 40.016944885 | 82.906776428 | PRO | 61 | h | 0.1000 | 265 |
| CG | 38.972518921 | 39.562160492 | 82.163795471 | PRO | 61 | c2 | -0.2000 | 266 |
| HG1 | 39.409160614 | 39.034259796 | 81.293624878 | PRO | 61 | h | 0.1000 | 267 |
| HG2 | 39.183399200 | 40.640045166 | 82.032295227 | PRO | 61 | h | 0.1000 | 268 |
| N | 38.213741302 | 35.753643036 | 81.804443359 | SER | 62 | n | -0.5000 | 269 |
| CA | 38.144962311 | 34.600208282 | 80.863403320 | SER | 62 | ca | 0.1200 | 270 |
| HN | 39.009967804 | 35.895751953 | 82.434890747 | SER | 62 | hn | 0.2800 | 271 |
| HA | 37.892318726 | 34.983673096 | 79.856529236 | SER | 62 | h | 0.1000 | 272 |
| C | 37.085021973 | 33.524326324 | 81.273231506 | SER | 62 | c' | 0.3800 | 273 |
| O | 37.382484436 | 32.625560760 | 82.070343018 | SER | 62 | o' | -0.3800 | 274 |
| CB | 39.569152832 | 33.994293213 | 80.760513306 | SER | 62 | c2 | -0.1700 | 275 |
| HB1 | 39.601100922 | 33.242229462 | 79.949050903 | SER | 62 | h | 0.1000 | 276 |
| HB2 | 40.317050934 | 34.759819031 | 80.475799561 | SER | 62 | h | 0.1000 | 277 |
| OG | 39.958038330 | 33.367904663 | 81.986091614 | SER | 62 | oh | -0.3800 | 278 |
| HG | 39.157264709 | 32.928077698 | 82.316406250 | SER | 62 | ho | 0.3500 | 279 |
| N | 35.853912354 | 33.643447876 | 80.748901367 | SER | 63 | n | -0.5000 | 280 |
| CA | 34.681579590 | 32.893772125 | 81.280097961 | SER | 63 | ca | 0.1200 | 281 |
| HN | 35.734226227 | 34.507610321 | 80.200576782 | SER | 63 | hn | 0.2800 | 282 |
| HA | 34.978878021 | 32.281963348 | 82.158424377 | SER | 63 | h | 0.1000 | 283 |
| C | 34.028987885 | 31.963005066 | 80.214485168 | SER | 63 | c' | 0.3800 | 284 |
| O | 33.624385834 | 32.404701233 | 79.134857178 | SER | 63 | o' | -0.3800 | 285 |
| CB | 33.674541473 | 33.937458038 | 81.815757751 | SER | 63 | c2 | -0.1700 | 286 |
| HB1 | 34.172107697 | 34.614356995 | 82.538948059 | SER | 63 | h | 0.1000 | 287 |
| HB2 | 33.303077698 | 34.594402313 | 81.003784180 | SER | 63 | h | 0.1000 | 288 |
| OG | 32.576236725 | 33.301517487 | 82.471984863 | SER | 63 | oh | -0.3800 | 289 |
| HG | 32.084590912 | 32.806625366 | 81.807708740 | SER | 63 | ho | 0.3500 | 290 |
| N | 33.852622986 | 30.677625656 | 80.556045532 | TRP | 64 | n | -0.5000 | 291 |
| CA | 33.070865631 | 29.709415436 | 79.732810974 | TRP | 64 | ca | 0.1200 | 292 |
| HN | 34.153343201 | 30.435497284 | 81.506057739 | TRP | 64 | hn | 0.2800 | 293 |
| HA | 33.375720978 | 29.840501785 | 78.676765442 | TRP | 64 | h | 0.1000 | 294 |
| C | 31.526346207 | 29.958730698 | 79.816452026 | TRP | 64 | c' | 0.3800 | 295 |
| O | 30.936735153 | 29.911306381 | 80.900970459 | TRP | 64 | o' | -0.3800 | 296 |
| CB | 33.498836517 | 28.253648758 | 80.086425781 | TRP | 64 | c2 | -0.2000 | 297 |
| HB1 | 32.936897276 | 27.550512314 | 79.442245483 | TRP | 64 | h | 0.1000 | 298 |
| HB2 | 34.548812866 | 25.110004425 | 79.767990112 | TRP | 64 | h | 0.1000 | 299 |
| CG | 33.372638702 | 27.788063049 | 81.551361084 | TRP | 64 | c5 | 0.0000 | 300 |
| CD1 | 32.236022949 | 27.198472977 | 82.145393372 | TRP | 64 | c5 | 0.0100 | 301 |
| NE1 | 32.442039490 | 26.926628113 | 83.513259888 | TRP | 64 | np | -0.5000 | 302 |
| CE2 | 33.734771729 | 27.365074158 | 83.750877380 | TRP | 64 | c5 | 0.1100 | 303 |
| CD2 | 34.313194275 | 27.885219574 | 82.565856934 | TRP | 64 | c5 | 0.0000 | 304 |
| HD1 | 31.308589935 | 27.011001587 | 81.622375488 | TRP | 64 | h | 0.1000 | 305 |
| HE1 | 31.781488419 | 26.532098770 | 84.192108154 | TRP | 64 | hn | 0.2800 | 306 |
| CE3 | 35.633460999 | 28.410655975 | 82.581642151 | TRP | 64 | cp | -0.1000 | 307 |
| HE3 | 36.086208344 | 28.812973022 | 81.686943054 | TRP | 64 | h | 0.1000 | 308 |
| CZ3 | 36.338203430 | 28.401332855 | 83.786201477 | TRP | 64 | cp | -0.1000 | 309 |
| HZ3 | 37.342418671 | 28.800062180 | 83.816780090 | TRP | 64 | h | 0.1000 | 310 |
| CH2 | 35.766292572 | 27.887487411 | 84.956939697 | TRP | 64 | cp | -0.1000 | 311 |
| HH2 | 36.336753845 | 27.895225525 | 85.875114441 | TRP | 64 | h | 0.1000 | 312 |
| CZ2 | 34.469055176 | 27.367534637 | 84.959693909 | TRP | 64 | cp | -0.1000 | 313 |
| HZ2 | 34.033626556 | 26.978828430 | 85.868453979 | TRP | 64 | h | 0.1000 | 314 |
| N | 30.884126663 | 30.253189087 | 78.672058105 | GLY | 65 | n | -0.5000 | 315 |
| CA | 29.433704376 | 30.582933426 | 78.625785828 | GLY | 65 | cg | 0.0200 | 316 |
| HN | 31.490442276 | 30.324731827 | 77.837860107 | GLY | 65 | hn | 0.2800 | 317 |

TABLE No. 2-continued

| Atom name | x | y | z | residue name and no. | | atom type, charge and no. | |
|---|---|---|---|---|---|---|---|
| HA1 | 29.049486160 | 30.927183151 | 79.604759216 | GLY | 65 | h | 0.1000 | 318 |
| HA2 | 29.301883698 | 31.462034225 | 77.967575073 | GLY | 65 | h | 0.1000 | 319 |
| C | 28.566276550 | 29.436250687 | 78.049354553 | GLY | 65 | c' | 0.3800 | 320 |
| O | 28.476503372 | 29.383417130 | 76.820671082 | GLY | 65 | o' | −0.3800 | 321 |
| N | 27.919076920 | 28.520057678 | 78.830680847 | PRO | 66 | n | −0.4200 | 322 |
| CA | 27.254581451 | 27.307062149 | 78.266265869 | PRO | 66 | ca | 0.0600 | 323 |
| HA | 28.007204056 | 26.749544144 | 77.674038860 | PRO | 66 | h | 0.1000 | 324 |
| CD | 27.931732178 | 28.547025681 | 80.307373047 | PRO | 66 | c2 | 0.0600 | 325 |
| HD1 | 27.674114227 | 29.536535263 | 80.727989197 | PRO | 66 | h | 0.1000 | 326 |
| HD2 | 28.930458069 | 28.264209747 | 80.693565369 | PRO | 66 | h | 0.1000 | 327 |
| C | 25.991449356 | 27.540506363 | 77.367637634 | PRO | 66 | c' | 0.3800 | 328 |
| O | 25.234470367 | 28.498056412 | 77.550445557 | PRO | 66 | o' | −0.3800 | 329 |
| CB | 26.947065353 | 26.487516403 | 79.540168762 | PRO | 66 | c2 | −0.2000 | 330 |
| HB1 | 26.021696091 | 25.883453349 | 79.467781067 | PRO | 66 | h | 0.1000 | 331 |
| HB2 | 27.765922546 | 25.768106461 | 79.730659485 | PRO | 66 | h | 0.1000 | 332 |
| CG | 26.879997253 | 27.505201340 | 80.680580139 | PRO | 66 | c2 | −0.2000 | 333 |
| HG1 | 25.878761292 | 27.974979401 | 80.732356567 | PRO | 66 | h | 0.1000 | 334 |
| HG2 | 27.057765961 | 27.053478241 | 81.674545288 | PRO | 66 | h | 0.1000 | 335 |
| N | 25.764133453 | 26.624628067 | 76.406608582 | CYS | 67 | n | −0.5000 | 336 |
| CA | 24.578670502 | 26.665664673 | 75.512832642 | CYS | 67 | ca | 0.1200 | 337 |
| HN | 26.474828720 | 25.893449783 | 76.320098877 | CYS | 67 | hn | 0.2800 | 338 |
| HA | 24.437746048 | 27.701400757 | 75.152099609 | CYS | 67 | h | 0.1000 | 339 |
| C | 23.256376266 | 26.130277634 | 76.174392700 | CYS | 67 | c' | 0.3800 | 340 |
| O | 23.219629288 | 24.940492630 | 76.516906738 | CYS | 67 | o' | −0.3800 | 341 |
| CB | 24.900175095 | 25.815908432 | 74.260444641 | CYS | 67 | c2 | −0.3000 | 342 |
| HB1 | 25.807971954 | 26.178848267 | 73.749794006 | CYS | 67 | h | 0.1000 | 343 |
| HB2 | 25.105169296 | 24.761932373 | 74.532623291 | CYS | 67 | h | 0.1000 | 344 |
| SG | 23.472158432 | 25.844451904 | 73.133270264 | CYS | 67 | s1 | 0.1000 | 345 |
| N | 22.124137878 | 26.895683289 | 76.264381409 | PRO | 68 | n | −0.4200 | 346 |
| CA | 20.786550522 | 26.297697067 | 76.529830933 | PRO | 68 | ca | 0.0600 | 347 |
| HA | 20.877141953 | 25.506265640 | 77.300582886 | PRO | 68 | h | 0.1000 | 348 |
| CD | 22.161409378 | 28.364057541 | 76.432929993 | PRO | 68 | c2 | 0.0600 | 349 |
| HD1 | 22.628620148 | 28.901371002 | 75.585960388 | PRO | 68 | h | 0.1000 | 350 |
| HD2 | 22.732339859 | 28.631174088 | 77.345329285 | PRO | 68 | h | 0.1000 | 351 |
| C | 20.190311432 | 25.593938828 | 75.255737305 | PRO | 68 | c' | 0.3800 | 352 |
| O | 20.566764832 | 24.451507568 | 74.984413147 | PRO | 68 | o' | −0.3800 | 353 |
| CB | 20.033475876 | 27.483673096 | 77.173645020 | PRO | 68 | c2 | −0.2000 | 354 |
| HB1 | 18.940057755 | 27.449979782 | 77.017181396 | PRO | 68 | h | 0.1000 | 355 |
| HB2 | 20.183664322 | 27.458950043 | 78.271354675 | PRO | 68 | h | 0.1000 | 356 |
| CG | 20.687761307 | 28.746078411 | 76.604209900 | PRO | 68 | c2 | −0.2000 | 357 |
| HG1 | 20.234010696 | 29.017192841 | 75.632743835 | PRO | 68 | h | 0.1000 | 358 |
| HG2 | 20.559530258 | 29.023554230 | 77.265640259 | PRO | 68 | h | 0.1000 | 359 |
| N | 19.297069550 | 26.226366043 | 74.460205078 | ARG+ | 69 | n | −0.5000 | 360 |
| CA | 18.727945328 | 25.594141006 | 73.229873657 | ARG+ | 69 | cd | 0.1200 | 361 |
| HN | 18.899488449 | 27.074655533 | 74.874603271 | ARG+ | 69 | hn | 0.2800 | 362 |
| HA | 19.468439102 | 24.889890671 | 72.798027039 | ARG+ | 69 | h | 0.1000 | 363 |
| C | 18.426181793 | 26.666866302 | 72.127845764 | ARG+ | 69 | c' | 0.3800 | 364 |
| O | 17.302417755 | 27.170328140 | 72.057907104 | ARG+ | 69 | o' | −0.3800 | 365 |
| CB | 17.487716675 | 24.741283417 | 73.645401001 | ARG+ | 69 | c2 | −0.2000 | 366 |
| HB1 | 17.790594101 | 24.038330078 | 74.447227478 | ARG+ | 69 | h | 0.1100 | 367 |
| HB2 | 16.742151260 | 25.409061432 | 74.119949341 | ARG+ | 69 | h | 0.1100 | 368 |
| CG | 16.806570053 | 23.930654526 | 72.510940552 | ARG+ | 69 | c2 | −0.2000 | 369 |
| HG1 | 16.500089645 | 24.624885559 | 71.702163696 | ARG+ | 69 | h | 0.1300 | 370 |
| HG2 | 17.539186478 | 23.235509872 | 72.053100586 | ARG+ | 69 | h | 0.1300 | 371 |
| CD | 15.574314117 | 23.148860931 | 73.007453918 | ARG+ | 69 | c2 | −0.0900 | 372 |
| HD1 | 15.890284538 | 22.374292374 | 73.738624573 | ARG+ | 69 | h | 0.1300 | 373 |
| HD2 | 14.902976036 | 23.843069077 | 73.554016113 | ARG+ | 69 | h | 0.1300 | 374 |
| NE | 14.865127563 | 22.521680832 | 71.855873108 | ARG+ | 69 | n1 | −0.5000 | 375 |
| HE | 15.293711662 | 22.507183075 | 70.926025391 | ARG+ | 69 | hn | 0.3600 | 376 |
| CZ | 13.645489693 | 21.980854034 | 71.902374268 | ARG+ | 69 | cr | 0.4500 | 377 |
| NH1 | 13.127552986 | 21.522832870 | 70.798370361 | ARG+ | 69 | n2 | −0.5000 | 378 |
| HH11 | 13.689088821 | 21.608518600 | 69.948852539 | ARG+ | 69 | hn | 0.3600 | 379 |
| HH12 | 12.188611031 | 21.122539520 | 70.853851318 | ARG+ | 69 | hn | 0.3600 | 380 |
| NH2 | 12.936479568 | 21.886768341 | 73.000465393 | ARG+ | 69 | n2 | −0.5000 | 381 |
| HH21 | 12.008401871 | 21.462900162 | 72.952354431 | ARG+ | 69 | hn | 0.3600 | 382 |
| HH22 | 13.405644417 | 22.251142502 | 73.831558228 | ARG+ | 69 | hn | 0.3600 | 383 |
| N | 19.430337906 | 26.966600418 | 71.273384094 | ARG+ | 70 | n | −0.5000 | 384 |
| CA | 19.316965103 | 27.784936905 | 70.016807556 | ARG+ | 70 | ca | 0.1200 | 385 |
| HN | 20.317523956 | 26.522169576 | 71.527793884 | ARG+ | 70 | hn | 0.2800 | 386 |
| HA | 19.139877319 | 27.013025284 | 69.241798401 | ARG+ | 70 | h | 0.1000 | 387 |
| C | 20.690151215 | 28.397680283 | 69.573341370 | ARG+ | 70 | c' | 0.3800 | 388 |
| O | 21.267679214 | 27.963806152 | 68.579154968 | ARG+ | 70 | o' | −0.3800 | 389 |
| CB | 18.103752136 | 28.753881454 | 69.796676636 | ARG+ | 70 | c2 | −0.2000 | 390 |
| HB1 | 18.134477615 | 29.133897781 | 68.754875183 | ARG+ | 70 | h | 0.1100 | 391 |
| HB2 | 17.183977127 | 28.135446548 | 69.816154480 | ARG+ | 70 | h | 0.1100 | 392 |

TABLE No. 2-continued

| Atom name | x | y | z | residue name and no. | | atom type, charge and no. | | |
|---|---|---|---|---|---|---|---|---|
| CG | 17.944366455 | 29.952959061 | 70.767364502 | ARG+ | 70 | c2 | −0.2000 | 393 |
| HG1 | 18.201717377 | 29.630409241 | 71.795295715 | ARG+ | 70 | h | 0.1300 | 394 |
| HG2 | 18.686578751 | 30.737569809 | 70.523498535 | ARG+ | 70 | h | 0.1300 | 395 |
| CD | 16.516407013 | 30.528032303 | 70.757499695 | ARG+ | 70 | c2 | −0.0900 | 396 |
| HD1 | 16.205293655 | 30.812314987 | 69.732498169 | ARG+ | 70 | h | 0.1300 | 397 |
| HD2 | 15.804359436 | 29.724859238 | 71.041206360 | ARG+ | 70 | h | 0.1300 | 398 |
| NE | 16.396289825 | 31.632083893 | 71.751823425 | ARG+ | 70 | n1 | −0.5000 | 399 |
| HE | 16.382929398 | 31.418577194 | 72.754409790 | ARG+ | 70 | hn | 0.3600 | 400 |
| CZ | 16.270032883 | 32.931114197 | 71.475357056 | ARG+ | 70 | cr | 0.4500 | 401 |
| NH1 | 16.119342804 | 33.758121490 | 72.470024109 | ARG+ | 70 | n2 | −0.5000 | 402 |
| HH11 | 16.097789764 | 33.352241516 | 73.407394409 | ARG+ | 70 | hn | 0.3600 | 403 |
| HH12 | 16.020824432 | 34.751869202 | 72.242614746 | ARG+ | 70 | hn | 0.3600 | 404 |
| NH2 | 16.295974731 | 33.427280426 | 70.262794495 | ARG+ | 70 | n2 | −0.5000 | 405 |
| HH21 | 16.191591263 | 34.436088562 | 70.142570496 | ARG+ | 70 | hn | 0.3600 | 406 |
| HH22 | 16.439420972 | 32.732715607 | 69.527351379 | ARG+ | 70 | hn | 0.3600 | 407 |
| N | 21.215826035 | 29.506198883 | 70.104598999 | TYRC | 71 | n | −0.5000 | 408 |
| HN | 21.692993164 | 29.961484909 | 69.319816589 | TYRC | 71 | hn | 0.2800 | 409 |
| CA | 22.037544250 | 29.469150543 | 71.348724365 | TYRC | 71 | ca | 0.1200 | 410 |
| HA | 22.727062225 | 28.601654053 | 71.296867371 | TYRC | 71 | h | 0.1000 | 411 |
| C | 21.230804443 | 29.295030594 | 72.663772583 | TYRC | 71 | c' | 0.4100 | 412 |
| OXT | 20.420524597 | 30.105148315 | 73.113685608 | TYRC | 71 | o' | −0.3800 | 413 |
| O | 21.522335052 | 28.107995987 | 73.273979187 | TYRC | 71 | oh | −0.3800 | 414 |
| HO | 20.994127274 | 28.000021444 | 74.066841125 | TYRC | 71 | ho | 0.3500 | 415 |
| CB | 22.938613892 | 30.740638733 | 71.402084351 | TYRC | 71 | c2 | −0.2000 | 416 |
| HB1 | 22.321226120 | 31.652799606 | 71.283157349 | TYRC | 71 | h | 0.1000 | 417 |
| HB2 | 23.363500595 | 30.853305817 | 72.420455933 | TYRC | 71 | h | 0.1000 | 418 |
| CG | 24.110603333 | 30.760416031 | 70.402580261 | TYRC | 71 | cp | 0.0000 | 419 |
| CD1 | 23.933057785 | 31.274461746 | 69.111869812 | TYRC | 71 | cp | −0.1000 | 420 |
| HD1 | 22.977622986 | 31.679159164 | 68.809974670 | TYRC | 71 | h | 0.1000 | 421 |
| CE1 | 24.985538483 | 31.264329910 | 68.201301575 | TYRC | 71 | cp | −0.1000 | 422 |
| HE1 | 24.833002090 | 31.650396347 | 67.203536987 | TYRC | 71 | h | 0.1000 | 423 |
| CZ | 26.227394104 | 30.757091522 | 68.577186584 | TYRC | 71 | cp | 0.0300 | 424 |
| OH | 27.265848160 | 30.762763977 | 67.686424255 | TYRC | 71 | oh | −0.3800 | 425 |
| HH | 26.966634750 | 31.154380798 | 66.863937378 | TYRC | 71 | ho | 0.3500 | 426 |
| CE2 | 26.415199280 | 30.251981735 | 69.859985352 | TYRC | 71 | cp | −0.1000 | 427 |
| HE2 | 27.377700806 | 29.852491379 | 70.147377014 | TYRC | 71 | h | 0.1000 | 428 |
| CD2 | 25.360828400 | 30.253871918 | 70.770927429 | TYRC | 71 | cp | −0.1000 | 429 |
| HD2 | 25.521846771 | 29.846044540 | 71.760574341 | TYRC | 71 | h | 0.1000 | 430 |

What is claimed is:

1. A composition comprising an antibody $G_1$ raised against an antigen selected from the group consisting of: LAG-3 (SEQ ID NO:1); soluble polypeptide fractions consisting of at least one of the four immunoglobulin type extracellular domains of the LAG-3 protein (amino acids 1–149, 150–239, 240–330 and 331–412 of SEQ ID NO:1); and a substituted LAG-3 or a substituted immunoglobulin type extracellular domain of LAG-3 consisting of amino acid residues 1–149, where one or more arginine residues at residue positions 73, 74 and 76 of SEQ ID NO:1 are substituted with glutamic acid residues.

2. A composition according to claim 1, wherein said antibody is a monoclonal antibody or an antigen-binding fragment thereof.

3. A composition according to claim 1, wherein said antibody fragment is an Fab, Fab' or F(ab')$_2$ fragment.

4. A composition according to claim 1, wherein said antibody or antigen-binding fragment thereof is bound to a cytotoxic molecule or a radioisotope.

5. A method of stimulating the immune system comprising administering to a subject in need of such treatment an immunostimulatory amount of an antibody raised against an antigen selected from the group consisting of: LAG-3; soluble polypeptide fractions consisting of at least one of the four immunoglobulin type extracellular domains of the LAG-3 protein (amino acids 1–149, 150–239, 240–330 and 331–412 of SEQ ID NO:1), a substituted LAG-3 or a substituted immunoglobulin type extracellular domain of LAG-3 consisting of amino acid residues 1–149, where one or more arginine residues at residue positions 73, 75 and 76 of SEQ ID NO:1 are substituted with glutamic acid residues.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 476 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60
```

-continued

```
Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
        210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Gly Pro Asp Leu Leu Val Thr
            275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln
            355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
                420                 425                 430

Thr Leu Gly Val Leu Ser Leu Leu Leu Leu Val Thr Gly Ala Phe Gly
            435                 440                 445

Phe His Leu Trp Arg Arg Gln Trp Arg Pro Arg Arg Phe Ser Ala Leu
        450                 455                 460

Glu Gln Gly Ile His Pro Arg Arg Leu Arg Ala Arg
465                 470                 475
```

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GCGCCTCGAG GCCCAGACCA TAGGAGAGAT GT                                 32

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GCGCAGATCT CTCCAGACCC AGAACAGTGA GGTTATACAT                         40

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCGCAGATCT ACCTGGGCTA GACAGCTCTG TGAA                               34

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGCCGTCGAC CGCTGCCCAG ACCATAGGAG AGATGTG                           37

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGCGTCGAC TTACATCGAG GCCTGGCCCA GGCGCAG                           37

(2) INFORMATION FOR SEQ ID NO:7:

(i) SEQUENCE CHARACTERISTICS:

-continued

```
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GCGCGTCGAC TTAACCCAGA ACAGTGAGGT TATAC                               35

(2) INFORMATION FOR SEQ ID NO:8:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

GCGCGTCGAC TTAACCTGGG CTAGACAGCT CTGTG                               35
```